US010939628B2

(12) United States Patent
Paz et al.

(10) Patent No.: US 10,939,628 B2
(45) Date of Patent: Mar. 9, 2021

(54) RESISTANCE TO TOLCNDV IN MELONS

(71) Applicant: Vilmorin & Cie, Paris (FR)

(72) Inventors: Zahi Paz, Berurim (IL); Emanuel Cohen, Berurim (IL); Imri Ben-Israel, Berurim (IL)

(73) Assignee: Vilmorin & Cie, Paris (FR)

( * ) Notice: Subject to any disclaimer, the term of this patent is extended or adjusted under 35 U.S.C. 154(b) by 153 days.

(21) Appl. No.: 16/066,593

(22) PCT Filed: Dec. 28, 2016

(86) PCT No.: PCT/EP2016/082740
§ 371 (c)(1),
(2) Date: Jun. 27, 2018

(87) PCT Pub. No.: WO2017/114848
PCT Pub. Date: Jul. 6, 2017

(65) Prior Publication Data
US 2020/0178485 A1 Jun. 11, 2020

(30) Foreign Application Priority Data

Dec. 30, 2015 (EP) .................................... 15307186

(51) Int. Cl.
*A01H 5/08* (2018.01)
*A01H 1/04* (2006.01)
*C12Q 1/6895* (2018.01)

(52) U.S. Cl.
CPC ................. *A01H 1/04* (2013.01); *A01H 5/08* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

PUBLICATIONS

Lopez et al 2015 Euphytica 204:679-691 (Year: 2015).*
Fauquet, C. M., et al, "Geminivirus strain demarcation and nomenclature", Arch. Virol. (2008), 153:783-821 (Exhibit 1);.
Garcia-Mas, J. et al., "The genome of melon (*Cucumis meo* L.)", Proc. Natl. Acad. Sci. USA 2012, 109(29):11872-7 (Exhibit 2);.
Islam, S. et al., "Screening of Luffa cylindrica Roem against tomato leaf curl New Delhi virus, inheritance of resistance and identification of SRAP markers linked to resistance gene", Journal of Horticulture Science and Biotechnology 2011, 86(6):661-667 (Exhibit 3);.
Lopez, C. et al., "Mechanical transmission of Tomato leaf curl New Delhi virus to cucurbit germplasm: selection of tolerance sources in *Cucumis melo*", Eupphytica 2015, 204:679-691 (Exhibit 4);.
Ruiz L. et al., "Analysis of the temporal and spatial disease progress of Bemisia tabaci-transmitted Cucurbit yellow stunting disorder virus and Cucumber vein yellowing virus in cucumber", Plant Pathology 2006, 55(2): 264-275 (Exhibit 5);.
Ruiz L. et al., "First Report of Tomato leaf curl New Delhi virus Infecting Tomato in Spain", Plant Disease 2015, 99(6):684 (Exhibit 6);.
Saeed M. et al., "A monopartite begomovirus-associated DNA beta satellite substitutes for the DNA B of a bipartite begomovirus to permit systemic infection", J Gen Virol. 2007, 88(Pt 10):2881-9 (Exhibit 7);.
Yazdani-Khameneh S et al., "Report of a new begomovirus on melon in Iran", New Disease Reports 2013, vol. 28, p. 17 (Exhibit 8); and.
Eppo Reporting Service : "European and Mediterranean plant protection organization", Jun. 1, 2015, pp. 1-21 (Exhibit 9).
International Search Report dated Jun. 1, 2017 in connection with PCT International Application No. PCT/EP2016/082740.
Written Opinion of the International Searching Authority dated Jun. 1, 2017 in connection with PCT International Application No. PCT/EP2016/082740.
S. Yazdani-Khameneh et al., "Report of a new begomovirus on melon in Iran", New Disease Reports, Dec. 19, 2013, vol. 28.
Eppo Reporting Service: "European and Mediterranean Plant Protection Organization", Jun. 1, 2015, pp. 1-21.
Fauquet, C. M., et al, "Geminivirus strain demarcation and nomenclature", Arch. Virol. (2008), 153:783-821.
Garcia-Mas, J. et al., "The genome of melon (*Cucumis melo* L.)", Proc. Natl. Acad. Sci. USA. 2012, 109(29):11872-7.
Islam, S. et al., "Screening of Luffa cylindrica Roem against tomato leaf curl New Delhi virus, inheritance of resistance and identification of SRAP markers linked to resistance gene", Journal of Horticulture Science and Biotechnology 2011, 86(6):661-667.
Lopez, C. et al., "Mechanical transmission of Tomato leaf curl New Delhi virus to cucurbit germplasm: selection of tolerance sources in *Cucumis melo*", Eupphytica 2015, 204:679-691.
Ruiz L. et al., "Analysis of the temporal and spatial disease progress of Bemisia tabaci-transmitted Cucurbit yellow stunting disorder virus and Cucumber vein yellowing virus in cucumber", Plant Pathology 2006, 55(2): 264-275.
Ruiz L. et al., "First Report of Tomato leaf curl New Delhi virus Infecting Tomato in Spain", Plant Disease 2015, 99(6):684.

(Continued)

*Primary Examiner* — Brent T Page
(74) *Attorney, Agent, or Firm* — John P. White

(57) ABSTRACT

The present invention is directed to melon plant and seed, namely of *C. melo* subsp. *melo*, which are resistant to ToLCNDV, comprising in their genome introgressed sequences from *C. melo* subsp. *agrestis* var. *acidulous* conferring resistance to said virus, when present homozygously. The introgressed sequences are preferably characterized by defined alleles of SNPs on chromosome 11, inter alia allele A of SNP Melon_sbg_14207_58 (SEQ ID No:9). The introgressed sequences can be chosen from those present in the genome of a plant of ToLR1 accession number NCIMB 42506. The invention is also directed to parts of these resistant plants, as well as progeny, to the use of these plants for introgressing the resistance in another genetic background, as well as to different methods for obtaining resistant melon plants or seeds.

20 Claims, 3 Drawing Sheets

Specification includes a Sequence Listing.

(56) References Cited

PUBLICATIONS

Saeed M. et al., "A monopartite begomovirus-associated DNA beta satellite substitutes for the DNA B of a bipartite begomovirus to permit systemic infection", J Gen Virol. 2007, 88(Pt 10):2881-9.

Yazdani-Khameneh S et al., "Report of a new begomovirus on melon in Iran", New Disease Reports 2013, vol. 28, p. 17.

Fauguet, C.M. et al., (2008) "Geminivirus Strain Demarcation and Nomenclature," Spring-Verlag.

López, Carmelo et al., (2015) "Mechanical transmission of Tomato leaf curl New Delhi virus to cucurbit germplasm: selection of tolerance sources in *Cucumis melo*," Springer Science+Business Media Dordrecht.

Extended European Search Report dated Mar. 31, 2016 by the European Patent Office in connection with counterpart European Application No. 15307186.5-1410.

* cited by examiner

RESISTANCE TO TOLCNDV IN MELONS

CROSS-REFERENCE TO RELATED APPLICATIONS

This application is a § 371 national stage of PCT International Application No. PCT/EP2016/082740, filed Dec. 28, 2016, claiming priority of European Patent Application No. 15307186.5, filed Dec. 30, 2015, the contents of each of which are hereby incorporated by reference into the application.

REFERENCE TO A SEQUENCE LISTING

This application incorporates-by-reference nucleotide and/or amino acid sequences which are present in the file named "180627_90579_Sequence_Listing_CAE.txt", which is 8.29 kilobytes in size, and which was created Jun. 26, 2018 in the IBM-PC machine format, having an operating system compatibility with MS-Windows, which is contained in the text file filed Jun. 27, 2018 as part of this application.

The present invention relates to resistance and/or tolerance in plants of *Cucumis melo* subsp. *melo* to geminiviruses, especially to begomoviruses, inter alia to Tomato leaf curl New Delhi virus (ToLCNDV). According to the invention, the resistance is provided by DNA sequences, introgressed from *Cucumis melo* subsp. *agrestis* var. *acidulus* at specific loci in the genome of a *Cucumis melo* subsp. *melo* plant. The introgressed sequences can be present homozygously or heterozygously in the genome of *Cucumis melo* subsp. *melo*, and when they are present homozygously, they confer resistance to said viruses.

BACKGROUND OF THE INVENTION

*Cucumis melo* is a member of the family Cucurbitaceae. The Cucurbitaceae is a family of about 100 genera and with 700 to 900 species depending of the authors, mostly of the tropics. The family includes pumpkins, squashes, gourds, watermelon, luffa and several weeds. The genus *Cucumis*, to which the cantaloupe, cucumbers, and several melons belong, includes about 70 species. *Cucumis melo* includes a wide range of cultivated plants, with a center of origin very probably in East Africa.

Melon has been divided in two subspecies, according to the hypanthium's hairiness: *Cucumis melo* subsp, *melo* with long and spreading hairs on the ovary or the young fruit and *Cucumis melo* subsp. *agrestis* with short and appressed hairs (Kirkbride, 1993). Botanical groups belonging to the *Cucumis melo* subsp. *agrestis* are found in eastern Asia, from India to Japan while *Cucumis melo* subsp. *melo* are more found from India to Europe and in the new world. Although crosses outside the species are sterile, intraspecific crosses are generally fertile, resulting in a confusing range of variation.

*Cucumis melo* subsp. *melo* comprises 11 types as cantalupensis (cantaloupe), *reticulatus* (muskmelon), adana, chandalak, ameri, inodorus (winter melon), *flexuosus* (snakemelon), chate, tibish, dudaim and chito (mango melon, garden melon) (Pitrat et al. 2000).

The *Cucumis melo* subsp. *agrestis* comprises 5 different groups: conomon (oriental pickling melon), makuwa, *chinensis, momordica* and *acidulus*.

*Cucumis melo* subsp. *agrestis* var. *acidulous* are generally monoecious plants, with oval or eliptic fruits, smooth, with a green or orange skin color, uniform or with spots. The flesh is white, very firm and crisp, without sugar or aroma.

*Cucumis melo* is a simple diploid species with twelve pairs of highly differentiated chromosomes. The *Cucumis melo* genome includes over 375 Mb of sequence with an estimated 27,427 protein-coding genes (Garcia-Mas et al., 2012).

A variety of pathogens affect the productivity of melon plants including viruses, fungi, bacteria, nematodes, and insects. Melons are inter alia susceptible to many viruses and virus resistance is therefore of major agricultural importance.

The taxonomic family Geminiviridae includes some of the most important plant viruses causing severe diseases in agricultural, ornamental and horticultural crops. Geminiviruses generally are characterized by the unique twin shape of a fused icosahedral viral particle. Geminiviruses are plant viruses which have ambisense single-stranded circular DNA genomes. The genome can either be a single component of 2500-3000 nucleotides, or two similar-sized components. They generally have an elongated, geminate capsid with two incomplete T=I icosahedra joined at the missing vertex. The capsids range from 18-20 nm in diameter with a length of about 30 nm. Viruses with bipartite genomes (begomoviruses only) have these components separated into two different particles, therefore more than one virus particle is required to infect a cell. Transmission of these viruses can be via leafhoppers (mastreviruses, curtoviruses) or via species of whitefly (begomoviruses) or via treehoppers (topocuviruses).

The geminiviruses are responsible for a significant amount of crop damage worldwide. Diseases caused by these viruses have long been recognized as a limitation to the cultivation of several important crops, including maize, cassava, bean, squash, cucurbits, and tomato. Epidemics of geminivirus diseases have arisen due to a number of factors, including the recombination of different geminiviruses co-infecting a plant, which enables novel, possibly virulent viruses to be developed. Other contributing factors include the transport of infected plant material to new locations, expansion of agriculture into new growing areas, and the expansion and migration of vectors that can spread the virus from one plant to another.

Geminiviruses comprise a large and diverse family of viruses that infect a wide range of important monocotyledonous and dicotyledonous crop species and cause significant yield losses. Geminiviruses are classified into four genera: genus Mastrevirus (e.g., Maize streak virus), genus Curtovirus (e.g., Beet curly top virus), genus Begomovirus (e.g., SLCV), and genus Topocuvirus (Tomato pseudo-curly top virus).

The genus Begomovirus contains more than 200 viral species (Fauquet et al, 2008) and belong to the taxonomic family Geminiviridae. They are plant viruses that as a group have a very wide host range. Natural hosts of begomoviruses are plant species in which the virus can replicate, cause systemic infection, and encapsidate, and from which virions are ingested and transmitted to a susceptible host by the whitefly vector (Funayama, 2001). Worldwide they are responsible for a large amount of economic damage to many important agronomic and horticultural crops such as tomatoes, beans, squash, cucurbits, cassava and cotton in subtropical and tropical regions of Americas, Africa and Asia. Begomoviruses cause stunting of plants, curling and yellowing of the leaves and low yield of fruits (Saeed et al. 2007). Morphologically, begomovirus particles are non-enveloped. The nucleocapsid is 38 nm long and 15-22 nm in diameter. While particles have basic isocahedral symmetry, they consist of two incomplete icosahedra—missing one vertex—joined together. There are 22 capsomeres per nucleocapsid. Begomovirus species has single stranded closed circular DNA. Most begomoviruses have a bipartite genome, meaning that the genome is segmented into two segments (referred to as DNA A and DNA B) that are packaged into separate particles. Both segments are generally required for successful symptomatic infection in a host cell, but DNA B is dependent for its replication upon DNA A, which can in some begomoviruses apparently cause infections on its own.

Tomato leaf curl New Delhi virus (ToLCNDV), a begomovirus, can cause severe losses in many crops. It was first described on tomatoes in India in 1995, but subsequently, many reports of damages to cucurbit crops have also been made, first in other Asian countries and more recently in Europe: in September 2012, symptoms have been observed on squash in Spain, first in Murcia region, then, by May 2013 in Almeria province, not anymore in squash but also on melon and pumpkins. Symptoms included curling and severe mosaic of the young leaves, very short internodes, fruit skin roughness and longitudinal cracking of the fruits, leading to catastrophic losses.

Current methods of preventing and controlling geminiviruses include controlling the spread of insect vectors that carry the virus, developing transgenic plants expressing the viral coat protein, and using classical breeding methods to develop plants having natural resistance to the virus. Disease resistant plants developed using classical plant breeding offer an effective, safe, and relatively less expensive method of controlling many crop diseases.

Islam et al. 2011 reported a monogenic dominant resistance in a breeding line of sponge gourd (*Luffa cylindrica* M. Roem). Such a resistance, of dominant nature, has however not be shown to be transferable to melon background.

Lopez et al 2015 conducted the first published screenings of cucurbit germplasm for the identification of tolerance sources. In general, all sources of *Cucumis melo* subsp. *melo* showed moderate to very severe symptoms and intermediate to high viral load, identifying them as improper resources for the finding of such resistances.

More interesting results were obtained when looking at *Cucumis melo* subsp. *agrestis*, as three accession of *Cucumis melo* subsp. *agrestis* var. *momordica* and some wild accessions from India, Ghana, Senegal and Zimbabwe had no or mild symptoms. Two of the tolerant *Cucumis melo* subsp. *agrestis* var. *momordica* had previously been reported to be resistant to potyviruses and used to introgress these resistances into commercial melon.

*Cucumis melo* subsp. *agrestis* var. *acidulous* was however not retained as a possible source by these authors as, after some delays in the symptoms appearance, they evolved to moderate to severe symptoms.

Moreover, in view of the traits of flesh qualities of *Cucumis melo* subsp. *agrestis* var. *acidulous* plants, namely a white/green flesh color, low brix, presence of fibers, cracking, absence of netting, no change of color prior maturity, these accessions were particularly unpromising introgression partner.

In spite of intensive work in this respect and the importance of melon production worldwide, currently, no *Cucumis melo* subsp. *melo* plants resistant or tolerant to ToLCNDV have been obtained through introgression of the trait from a wild species.

Therefore, there is an important need in the art to identify a reliable monogenic source of resistance and/or tolerance which could then be used to obtain resistant commercial plants of *Cucumis melo* subsp. *melo*.

The present invention provides *C. melo* subsp. *melo* plants that display resistance and/or tolerance to Tomato leaf curl New Delhi virus (ToLCNDV), as well as methods that produce or identify melon plants that display resistance and/or tolerance to Tomato leaf curl New Delhi virus (ToLCNDV), and potentially also to other geminiviruses. The present invention also discloses molecular genetic markers, especially SNPs, linked to the recessive genetic locus conferring resistance and/or tolerance to ToLCNDV.

SUMMARY

The present inventors have identified a wild *C. melo* subsp. *agrestis* var. *acidulous* which displays a high level of resistance to ToLCNDV and they have been able to introgress, into *C. melo* subsp. *melo* genetic background, the *C. melo* subsp. *agrestis* var. *acidulous* sequences conferring resistance to ToLCNDV, thus obtaining resistant *Cucumis melo* subsp. *melo* plants. The resistance of the present invention is imparted by the newly discovered sequences conferring resistance, said resistance being of monogenic and recessive nature. Said resistance is easily transferable to different genetic backgrounds, due to its monogenic nature. Moreover, this resistance can be transferred without linked negative traits, especially unlinked to negative commercial traits such as poor flesh qualities or low brix below 6 or 7.

The present invention thus provides these introgressed sequences from *C. melo* subsp. *agrestis* var. *acidulous* conferring, when present in the homozygous state, the phenotype of resistance/tolerance to ToLCNDV. The invention also provides *Cucumis melo* subsp. *melo* plants that display important resistance to geminiviruses, especially resistance to ToLCNDV, as well as methods that produce or identify *Cucumis melo* subsp. *melo* plants or populations (germplasm) that display resistance to ToLCNDV infection, as well as seeds, fruits and other plant parts such as pollen and ovules containing the introgressed sequences conferring the resistance. The present invention also discloses molecular genetic markers, especially SNPs, linked to the introgressed sequences conferring resistance, i.e. to the resistance locus also called resistance gene, which is of recessive nature.

Definitions

The term "Degree brix" or "brix" indicates the soluble solid content of an aqueous solution inter alia of a juice, the vast majority of which being sugars. These are mostly estimated by a refractometer and measured as degrees Brix. The higher the degree, the more sugar content. The brix measurement is important to assess melon taste as fruits with low brix and therefore poor sugar content will not be appreciated by customers.

The term "Resistance" is as defined by the ISF (International Seed Federation) Vegetable and Ornamental Crops Section for describing the reaction of plants to pests or pathogens, and abiotic stresses for the Vegetable Seed Industry.

Specifically, by resistance, it is meant the ability of a plant variety to restrict the growth and development of a specified pest or pathogen and/or the damage they cause when compared to susceptible plant varieties under similar environmental conditions and pest or pathogen pressure. Resistant varieties may exhibit some disease symptoms or damage under heavy pest or pathogen pressure.

The term 'Tolerance' is used herein to indicate a phenotype of a plant wherein disease-symptoms remain absent upon exposure of said plant to an infective dosage of virus, whereby the presence of a systemic or local infection, virus multiplication, at least the presence of viral genomic sequences in cells of said plant and/or genomic integration thereof can be established. Tolerant plants are therefore resistant for symptom expression but symptomless carriers of the virus. Sometimes, viral sequences may be present or even multiply in plants without causing disease symptoms.

Susceptibility: The inability of a plant variety to restrict the growth and development of a specified pest or pathogen.

A *Cucumis melo* subsp. *melo* plant susceptible to ToLCNDV, is for example the commercially available variety *C. melo* subsp. *melo* Vedrantais. All commercially available varieties of melons are, to date, susceptible to ToLCNDV, before the present invention.

A plant according to the invention has thus at least improved resistance to ToLCNDV, with respect to the variety Vedrantais, and more generally with respect to any commercial variety of melon. The resistance of the invention is a resistance to the ToLCNV, especially to the severe strains, giving rise to the more severe symptoms.

As used herein, the term "offspring" or "progeny" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "heterozygote" refers to a diploid or polyploid individual cell or plant having different alleles (forms of a given gene or sequences) present at least at one locus.

As used herein, the term "heterozygous" refers to the presence of different alleles (forms of a given gene or sequences) at a particular locus.

As used herein, homologous chromosomes, or homologs (or homologues), refer to a set of one maternal and one paternal chromosomes that pair up with each other during meiosis. These copies have the same genes in the same loci and the same centromere location.

As used herein, the term "homozygote" refers to an individual cell or plant having the same alleles at one or more loci on all homologous chromosomes.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "locus" (plural: "loci") refers to any site that has been defined genetically. A locus may be a gene, or part of a gene, or a DNA sequence, and may be occupied by different sequences. A locus may also be defined by a SNP (Single Nucleotide Polymorphism), or by several SNPs.

The invention encompasses plants of different ploidy levels, whether a diploid plant, but also a triploid plant, a tetraploid plant, etc.

By introgression, it is meant the infiltration of the genes or of genomic sequences of one species or subspecies into the gene pool of another one from an initial interspecific hybrid between these species or subspecies.

DETAILED DESCRIPTION OF THE INVENTION

The present invention is directed to *C. melo* subsp. *melo* plants that display important resistance to geminiviruses, and more specifically resistance to ToLCNDV, as well as methods that produce or identify *C. melo* subsp. *melo* plants that display resistance to ToLCNDV infection. The present invention also discloses molecular genetic markers, especially SNPs, linked to the resistance loci.

It is to be noted that, whereas the phenotype of interest according to the invention is mainly referred to, in the present description, as "resistance" to ToLCNDV or geminiviruses, the invention is directed to resistance and/or tolerance to ToLCNDV or geminiviruses, insofar as, depending on the specific infection conditions, both phenotypes may be observed on the plants.

In any case, for the plants of the invention, there are however at least some infection conditions in which the phenotype can be classified as resistance according to the ISF definition given above. Plants of the invention may also behave as symptomless carriers, under certain conditions.

The resistance and/or tolerance according to the invention is preferably in response to any type of infection, either natural infection or mechanical inoculation, and in any event a resistance and/or tolerance to natural infection by ToLCNDV.

The resistance and/or tolerance according to the invention is preferably characterized by the absence of all the symptoms generally associated to ToLCNDV infection, especially severe ToLCNDV, namely leaves in upper part of plant showing yellowing mosaic, puckering and stunting of the plant, upon exposure to the virus, in natural infection conditions.

The seeds and plants according to the invention have been obtained from an initial inter-subspecies cross between a plant of *C. melo* subsp. *agrestis* var. *acidulous* H-MLCND-32, the introgression partner displaying the phenotype of interest, and a plant of an inbred line of *C. melo* subsp. *melo* Vedrantais, the recurrent susceptible parent. Seeds of recombinant inbred lines, phenotyped in example 10 of the experimental section, deriving from this initial cross, homozygously resistant to ToLCNDV, called ToLR1, have been deposited by the inventors at the NCIMB under the accession number NCIMB 42506 on 23 Dec. 2015. The plants grown from these deposited seeds are plants resistant to ToLCNDV, and have moreover a round or round-oval fruit shape, a brix of at least 9 and an orange flesh color, with possibly patches of cream color.

According to a first aspect, the present invention is thus directed to a *C. melo* subsp. *melo* plant or seed, which is resistant and/or tolerant to ToLCNDV, comprising in its genome introgressed sequences or interval from *C. melo* subsp. *agrestis* var. *acidulous* conferring said resistance and/or tolerance to ToLCNDV. Said sequences introgressed from *C. melo* subsp. *agrestis* var. *acidulous* confer the resistance to a *C. melo* subsp. *melo* plant or seed only when present homozygously in the *C. melo* subsp. *melo* genome. The invention is also directed to a cell of such a plant or seed, comprising these introgressed sequences.

The introgressed interval acts as a single recessive allele of a resistance gene responsible for the phenotype (i.e. the resistance trait is monogenic); the F1 generation arising from a cross between a resistant plant and a susceptible plant will thus not display the desired phenotype of ToLCNDV resistance, as illustrated in example 6. Only a plant homozygous for the introgressed interval will fully exhibit the ToLCNDV resistance phenotype. This phenotype can be used to identify progeny that are homozygous for the claimed introgressed sequences or interval. As mentioned above, the resistance phenotype may, under certain circumstances, be also qualified as tolerance to ToLCNDV. The introgressed interval acting as a resistance gene confers the phenotype of interest and is unlinked to negative features incompatible with marketability of the plants or fruit, inter alia poor brix below 6 or 7, or white green flesh color.

The resistance phenotype can be tested as described in examples 1 and 2 of the experimental section, i.e. by natural infection or by mechanical inoculation.

The introgressed sequences are preferably to be found on chromosome 11 in the *C. melo* subsp. *melo* genome and thus confer resistance and/or tolerance to ToLCNDV when they are present on both homologous chromosomes 11, or on all the homologous chromosomes 11 if the plant has more than two sets of chromosomes, i.e. on all chromosomes 11 present in the genome of the plant.

The introgressed sequences conferring the resistance are more preferably located within the chromosomal region of chromosome 11 which is delimited on one side by the SNP Melon_sbg_617_42 (SEQ ID No:1), and on the other side by the SNP Melon_sbg_16835_17 (SEQ ID No:16).

The specific polymorphisms corresponding to the SNPs (Single Nucleotide Polymorphism) referred to in this description, as well as the flanking sequences of these SNPs in the *C. melo* genome, are given in the experimental section, table 4 and accompanying sequence listing, as well as their position in the melon genome sequence built (Garcia-Mas et al, 2012).

It is to be noted in this respect that, by definition, a SNP refers to a single isolated nucleotide in the genome, which is variable depending on the allele which is present, whereas the flanking nucleotides are identical. For ease of clear identification of the position of the different SNPs, their position is given in table 4, by reference to the position in the melon genome sequence build and by reference to their flanking sequences, identified by SEQ ID number. In the sequence associated with a specific SNP in the present application, for example SEQ ID No:1 for the SNP Melon_sbg_617_42, only one nucleotide within the sequence actually corresponds to the polymorphism, namely the nucleotide having the position identified by the last number of the SNP name, e.g. the $42^{nd}$ nucleotide of SEQ ID No:1 corresponds to the polymorphic position SNP Melon_sbg_617_42. The flanking sequences are given for positioning the SNP in the genome but are not part of the polymorphism as such.

The introgressed sequences or interval conferring the resistance or tolerance are preferably chosen from the introgressed sequences from *C. melo* subsp. *agrestis* var. *acidulous* present in the genome of a plant of ToLR1, representative seeds of which are deposited at the NCIMB under the accession number NCIMB 42506. They are especially chosen from the introgressed sequences from *C. melo* subsp. *agrestis* var. *acidulous* present on chromosome 11 of said NCIMB 42506. Indeed, the deposited seeds comprise, on both homologous chromosomes 11, introgressed sequences from *C. melo* subsp. *agrestis* var. *acidulous* H-MLCND-32, i.e. from the introgression partner displaying the phenotype of interest, wherein said introgressed sequences are also conferring the phenotype in *C. melo* subsp. *melo* genetic background. A sample of this ToLR1 seed has been deposited by Hazera Seeds Ltd, Berurim, M. P. Shikmim 79837, Israel, pursuant to, and in satisfaction of, the requirements of the Budapest Treaty on the International Recognition of the Deposit of Microorganisms for the Purposes of Patent Procedure (the "Budapest treaty") with the National Collection of Industrial, Food and Marine Bacteria (NCIMB), (NCIMB Ltd, Ferguson Building, Craibstone Estate, Bucksburn, Aberdeen AB21 9YA, United Kingdom), on 23 Dec. 2015, under accession number NCIMB 42506. The deposited seeds are not from a plant variety.

A deposit of this ToLR1 seed is maintained by Hazera Seeds Ltd, Berurim, M. P. Shikmim 79837, Israel.

The sequences conferring the resistance are present on both homologous chromosomes 11 of all deposited seeds; as such the genome of these deposited seeds represent a reservoir of introgressed sequences from *C. melo* subsp. *agrestis* var. *acidulous* in the *C. melo* subsp. *melo* genome conferring resistance to ToLCNDV according to the invention. A plant or seed of the invention comprises in its genome introgressed sequences from *C. melo* subsp. *agrestis* var. *acidulous*, namely from H-MLCND-32 which are chosen from this reservoir, and can thus be found in this reservoir.

Whereas all deposited seeds possess an introgressed fragment at the same locus and conferring the phenotype according to the invention, this introgressed fragment may vary in length between the deposited seeds.

The present invention is thus also directed to a *C. melo* subsp. *melo* seed, plant or cell having in its genome introgressed sequences from *C. melo* subsp. *agrestis* var. *acidulous* conferring resistance to ToLCNDV, wherein said introgressed sequences conferring the resistance are chosen from the introgressed sequences from *C. melo* subsp. *agrestis* var. *acidulous* present in the genome of a seed of ToLR1 corresponding to NCIMB 42506 deposit. This resistance is conferred only when said sequences are present homozygously. Said introgressed sequences or intervals may form part of larger introgression fragments from *C. melo* subsp. *agrestis* var. *acidulous* into the genome of a *C. melo* subsp. *melo* plant of the invention.

By "introgressed sequences or intervals from *C. melo* subsp. *agrestis* var. *acidulous* at a given locus" or "introgressed sequences or intervals from *C. melo* subsp. *agrestis* var. *acidulous* present/found at a given locus", it is to be understood that the genomic interval found at this given locus has the same sequence as the corresponding genomic interval found in the *C. melo* subsp. *agrestis* var. *acidulous* donor, i.e. in the introgression partner, at the same locus and also the same sequence as the corresponding genomic interval found in ToLR1 (NCIMB 42506) at the same locus. By having the "same sequence", it means that the two sequences to be compared are identical to the exception of potential point mutations which may occur during transmission of the genomic interval to progeny, i.e. preferably at least 99% identical on a length of 1 kbase. It can be deduced that a genomic interval under test has the same sequence, in the sense of the invention, as the corresponding genomic interval found in the *C. melo* subsp. *agrestis* var. *acidulous* donor at the same locus, if said genomic interval under test is also capable of conferring resistance to ToLCNDV.

The presence of introgressed sequences into the genome of a *C. melo* subsp. *melo* plant, seed or cell may for example be shown by GISH (genetic in situ hybridization). GISH is indeed a powerful technique for detection of the introgression of chromatin material from one species or subspecies onto another species or subspecies. The advantage of GISH is that the introgression process is visualized by means of 'pictures of the introgressed genome'. With this technique, it is also possible to establish if a particular region of the genome is homozygous or heterozygous, thanks to the use of molecular cytogenetic markers which are co-dominant. By this technique, it is also possible to determine in which chromosome an introgressed gene of interest is present. According to a preferred embodiment, the introgressed sequences conferring the resistance to a *C. melo* subsp. *melo* plant or seed of the invention, and which are also to be found in the genome of the deposited seeds, are introgressed on chromosome 11 of a plant according to the invention, and more precisely within the chromosomal region of chromosome 11 delimited on one side by the Melon_sbg_617_42 (SEQ ID No:1), and on the other side by the Melon_sbg_16835_17 (SEQ ID No:16), preferably within the first sub-region delimited by Melon_sbg_33761_74 (SEQ ID No:7) and Melon_sbg_16835_17, and even more preferably within the second sub-region delimited on one side by the Melon_sbg_33761_74 and on the other side by the Melon_sbg_22016_36 (SEQ ID No 12).

In other words, in the genome of a *C. melo* subsp. *melo* plant, seed or cell of the invention, the section of chromosome 11 within the region and/or sub-regions mentioned above, comprises sequences which are of *C. melo* subsp. *agrestis* var. *acidulous* origin. These sequences are responsible for the ToLCNDV resistance, in both *C. melo* subsp. *agrestis* var. *acidulous* and *C. melo* subsp. *melo* genetic backgrounds.

According to a preferred embodiment, the chromosomal regions mentioned above, and preferably the region delimited on one side by Melon_sbg_33761_74 and on the other side by Melon_sbg_22016_36, exclusively comprise or correspond to introgressed sequences from *C. melo* subsp. *agrestis* var. *acidulous*. According to this embodiment, in a plant, seed or cell of the invention, the genomic fragment of said regions, and especially of the region within the positions corresponding to Melon_sbg_33761_74 and Melon_sbg_22016_36, is an introgression fragment from *C. melo* subsp. *agrestis* var. *acidulous* and therefore has the same sequence as the genomic fragment delimited by the same SNPs in the deposited seeds.

It is noted in this respect that specific positions in a chromosome can indeed be defined with respect to single nucleotide polymorphism, insofar as the flanking sequences of said SNPs are defined in order to unambiguously position them on the genome. The present inventors have used SNPs, identified by their flanking sequences, present in the subspecies *melo* and subspecies *agrestis* genomes, to discriminate between introgressed and endogenously residing sequences and to track down the introgressed sequences from *C. melo* subsp. *agrestis* var. *acidulous* in the *C. melo* subsp. *melo* genome.

A chromosomal region delimited by two SNPs X and Y refers to the section of the chromosome lying between the positions of these two SNPs and comprising said SNPs, therefore the nucleotide sequence of this chromosomal region begins with the nucleotide corresponding to SNP X and ends with the nucleotide corresponding to SNP Y, i.e. the SNPs are comprised within the region they delimit, in the sense of the invention.

The present inventors have identified that introgressed sequences essential for the phenotype of interest are to be found in the chromosomal region mentioned above, by identifying the presence of introgressed sequences at different loci along said regions, namely at 16 different loci defined by the 16 following SNPs: Melon_sbg_617_42, Melon_sbg_617_84, Melon_sbg_20578_63, Melon_sbg_20578_82, Melon_sbg_55680_17, Melon_sbg_60684_74, Melon_sbg_33761_74, Melon_sbg_2720_78, Melon_sbg_14207_58, Melon_sbg_22016_27, Melon_sbg_22016_30, Melon_sbg_22016_36, Melon_sbg_11556_13, Melon_sbg_24259_45, Melon_sbg_16835_5 and Melon_sbg_16835_17. The presence of introgressed sequences from *C. melo* subsp. *agrestis* var. *acidulous* at these loci is thus indicative of a resistance to ToLCNDV phenotype. These 16 SNPs are referred to herewith as the 16 SNPs of the invention. Therefore, according to another embodiment of the invention, the introgressed sequences present in the genome of a plant, seed or cell of the invention are preferably to be found at least at one or more of the 16 loci encompassing said 16 SNPs mentioned above, for example at 2, 3, 4, 8, 10 or 12 of these 16 loci, or at all of them.

More preferably, introgressed sequences are to be found in the sub-region delimited by SNPs Melon_sbg_33761_74 and SNP Melon_sbg_16835_17, and thus at least at one of the 10 loci corresponding to the loci encompassing one of the 10 SNPs Melon_sbg_33761_74, Melon_sbg_2720_78, Melon_sbg_14207_58, Melon_sbg_22016_27, Melon_sbg_22016_30, Melon_sbg_22016_36, Melon_sbg_11556_13, Melon_sbg_24259_45, Melon_sbg_16835_5 and Melon_sbg_16835_17. These 10 SNPs are referred herewith as the 10 preferred SNPs of the invention. Introgressed sequences are preferably to be found at least at 2, 3, 4, 8 of these 10 loci, or at all of them.

Even more preferably, the introgressed sequences from *C. melo* subsp. *agrestis* var. *acidulous* present in the genome of a plant or seed of the invention are preferably to be found at least at one or more of the following loci, located within the sub-region delimited by SNPs Melon_sbg_33761_74 and SNP Melon_sbg_22016_36:

locus encompassing SNP Melon_sbg_33761_74 and/or
locus encompassing SNP Melon_sbg_2720_78 and/or
locus encompassing SNP Melon_sbg_14207_58 and/or
locus encompassing SNP Melon_sbg_22016_27, and/or
locus encompassing SNP Melon_sbg_22016_30 and/or
locus encompassing SNP Melon_sbg_22016_36.

It is to be noted that the three SNPs Melon_sbg_22016_27 (SEQ ID No:10), SNP Melon_sbg_22016_30 (SEQ ID No:11) and SNP Melon_sbg_22016_36 (SEQ ID No:12) are only 3 nucleotides away from each other, such that they are generally transmitted en bloc, as an haplotype, therefore if introgressed sequences are to be found at one of these 3 loci, they are also to be found at the other 2. Introgressed sequences, conferring the resistance phenotype are thus to be found at one or more of the following loci:

locus encompassing SNP Melon_sbg_33761_74 and/or
locus encompassing SNP Melon_sbg_2720_78 and/or
locus encompassing SNP Melon_sbg_14207_58 and/or
locus encompassing SNPs Melon_sbg_22016_27, Melon_sbg_22016_30 and Melon_sbg_22016_36.

In a plant, seed or cell of the invention, the presence of the introgressed sequences conferring the phenotype of interest is thus characterized by at least one marker selected from the group consisting of SNP Melon_sbg_33761_74, SNP Melon_sbg_2720_78, SNP Melon_sbg_14207_58, SNP Melon_sbg_22016_27, SNP Melon_sbg_22016_30 and SNP Melon_sbg_22016_36, preferably by at least 2, 3, 4 or 5 markers chosen from this group. When the introgressed sequences from C. melo subsp. agrestis var. acidulous conferring the resistance (or tolerance, depending on the conditions) are found in a locus encompassing a given SNP, this means that the allele of this SNP is the allele found in the wild C. melo subsp. agrestis var. acidulous introgression partner H-MLCND-32 and also in the deposited resistant ToLR1 (NCIMB 42506). This also means that the 5' flanking region of said SNPs, or the 3' flanking region of said SNP, or both regions, are also identical to C. melo subsp. agrestis var. acidulous sequences in this region. Therefore, this given SNP may form part of the 3' border or 5' border of the introgressed interval, or may be within the introgressed interval conferring the desired phenotype.

The alleles of the 16 SNPs of the invention corresponding to the alleles of the C. melo subsp. agrestis var. acidulous conferring the resistance, are: allele T of Melon_sbg_617_42, allele G of Melon_sbg_617_84, allele A of Melon_sbg_20578_63, allele C of Melon_sbg_20578_82, allele A of Melon_sbg_55680_17, allele A of Melon_sbg_60684_74, allele T of Melon_sbg_33761_74, allele G of Melon_sbg_2720_78, allele A of Melon_sbg_14207_58, allele G of Melon_sbg_22016_27, allele G of Melon_sbg_22016_30, allele G of Melon_sbg_22016_36, allele C of Melon_sbg_11556_13, allele C of Melon_sbg_24259_45, allele T of Melon_sbg_16835_5, and allele T of Melon_sbg_16835_17. The presence of the introgressed sequences of interest can be revealed by the presence of said specific alleles, characteristic of the resistant introgression partner, and distinct from the allele of the recurrent C. melo subsp melo parent for these SNPs. The alleles of these SNPs can thus reflect the presence of the introgression sequences of the invention.

According to a preferred embodiment, introgressed sequences from C. melo subsp. agrestis var. acidulous conferring the resistance (or tolerance, depending on the conditions) are found in a locus encompassing Melon_sbg_14207_58. The allele of SNP Melon_sbg_14207_58 in the genome of a plant, seed or cell of the invention is thus the allele of this SNP found in the wild introgression partner H-MLCND-32 and also in the deposited resistant ToLR1, i.e. allele A of Melon_sbg_14207_58. The 5' flanking region of said SNP, or the 3' flanking region of said SNP, or both regions, are preferably also identical to C. melo subsp. agrestis var. acidulous sequences in this region. Therefore, the SNP Melon_sbg_14207_58 may form part of the 3' border or 5' border of the introgressed interval, but preferably this SNP is within the introgressed interval conferring the desired phenotype.

According to a preferred embodiment, the introgressed sequences present in the genome of a plant, seed or cell of the invention are to be found at one or two of the following loci:

locus encompassing SNP Melon_sbg_33761_74 and
locus encompassing SNP Melon_sbg_2720_78;
in addition or in place of the introgressed sequences found at the locus encompassing Melon_sbg_14207_58 according to the previous embodiment.

These three SNPs Melon_sbg_33761_74, Melon_sbg_2720_78 and Melon_sbg_14207_58 are indeed those having the best predictive value for the phenotype of interest.

According to a preferred embodiment, introgressed sequences from C. melo subsp. agrestis var. acidulous are to be found in a chromosomal segment including and encompassing the three SNPs Melon_sbg_33761_74, Melon_sbg_2720_78 and Melon_sbg_14207_58, i.e. the region delimited by Melon_sbg_33761_74 and Melon_sbg_14207_58 is an introgression fragment from C. melo subsp. agrestis var. acidulous.

Preferably, introgressed sequences from C. melo subsp. agrestis var. acidulous are also found at the locus encompassing SNPs Melon_sbg_22016_27, Melon_sbg_22016_30 and Melon_sbg_22016_36.

Consequently, a resistant plant, seed or cell of the invention may also be characterized by the homozygous allele A of Melon_sbg_14207_58 (SEQ ID No:9), or homozygous allele T of Melon_sbg_33761_74 (SEQ ID No:7), or homozygous allele G of Melon_sbg_2720_78 (SEQ ID No:8), or two or all of them. They may also be characterized in addition by allele G of SNPs Melon_sbg_22016_27, Melon_sbg_22016_30 and Melon_sbg_22016_36.

The presence of the introgressed sequences can also be revealed by genic amplification of sequences within the regions delimited by the SNPs of the invention, preferably the region delimited by Melon_sbg_33761_74 and Melon_sbg_22016_36, or by genic amplification of sequences in the proximity of the SNPs defined in the present invention, preferably Melon_sbg_33761_74, Melon_sbg_2720_78 and Melon_sbg_14207_58, and preferably Melon_sbg_14207_58, followed by comparison with the sequence of the respective amplification fragment, obtainable by carrying out the same genic amplification on seeds deposited at the NCIMB under accession number NCIMB 42506. Primers for the genic amplification can be defined by use of the flanking sequences disclosed in the present invention, potentially in combination with the available C. melo genome assembly.

Preferably, the introgressed sequences conferring the phenotype of interest, i.e. resistance or tolerance, are in linkage disequilibrium with the allele of Melon_sbg_14207_58, and more preferably with the alleles of the three SNPs Melon_sbg_33761_74, Melon_sbg_2720_78 and Melon_sbg_14207_58. Linkage disequilibrium indeed is used to describe common inheritance of genomic sequences in a cross population analysis when no linkage exists. Linkage describes common inheritance of genomic sequences in a population structure pending on the frequency of recombination.

The linkage disequilibrium score may be any positive score, meaning that the association of one or all of SNPs Melon_sbg_33761_74, Melon_sbg_2720_78 and Melon_sbg_14207_58 with the introgressed sequences is not random.

In a plant, seed or cell of the invention, thus comprising in its genome introgressed sequences from C. melo subsp.

*agrestis* var. *acidulous*, said introgressed sequences are preferably to be found in the genome at a genetic distance of less than 20 cM, preferably less than 15 cM, most preferably less than 10 cM, and even preferably less than 5 cM from the locus corresponding to SNP Melon_sbg_14207_58.

According to an embodiment, a seed, plant or cell of the invention is characterized by the presence of allele A of Melon_sbg_14207_58 on chromosome 11, in combination with absence of allele C of said SNP. Indeed, presence of allele A of said SNP confirms the presence of introgressed sequences from *C. melo* subsp. *agrestis* var. *acidulous* at the locus of Melon_sbg_14207_58; moreover the absence of allele C confirms that the introgressed sequences are homozygously present, i.e. present on both homologs of chromosome 11.

According to another embodiment, a seed, plant or cell of the invention is characterized by the presence of allele G of SNP Melon_sbg_2720_78, in combination with absence of allele A of said SNP. Indeed, presence of allele G of this SNP confirms the presence of introgressed sequences from *C. melo* subsp. *agrestis* var. *acidulous* at the locus of SNP Melon_sbg_2720_78; moreover the absence of allele A confirms that the introgressed sequences are homozygously present.

According to still another embodiment, a seed, plant or cell of the invention is characterized by the presence of allele T of SNP Melon_sbg_33761_74, in combination with absence of allele C of said SNP.

In a preferred embodiment, in a genome of a plant, seed or cell of the invention, allele A of Melon_sbg_14207_58, allele G of SNP Melon_sbg_2720_78 and allele T of Melon_sbg_33761_74 are simultaneously present, and the other alleles of these SNP are absent, namely alleles C, A and C respectively are absent.

In still another embodiment, a plant, cell or seed of the invention is characterized by:
  the presence of allele T of Melon_sbg_33761_74 combined with the absence of allele C for this SNP; and/or
  the presence of allele G of Melon_sbg_2720_78 combined with the absence of allele A for said SNP; and/or
  the presence of allele A of Melon_sbg_14207_58 combined with the absence of allele C for said SNP; and/or
  the presence of allele G of Melon_sbg_22016_27 combined with the absence of allele C for said SNP; and/or
  the presence of allele G of Melon_sbg_22016_30 combined with the absence of allele A for said SNP; and/or
  the presence of allele G of Melon_sbg_22016_36 combined with the absence of allele A for said SNP.

In another embodiment, in the genome of a *C. melo* subsp. *melo* plant, seed or cell of the invention, the introgressed sequences are preferably to be found strictly within a chromosomal interval of chromosome 11, boundaries excluded, wherein said boundaries correspond to the location of Melon_sbg_33761_74 (SEQ ID No:7) on one side and to the location of Melon_sbg_22016_36 (SEQ ID No:12) on the other side, meaning that the allele of Melon_sbg_33761_74 and the allele of Melon_sbg_22016_36 are the alleles representative of *C. melo* subsp. *melo* sequences, i.e. not introgressed sequences.

Preferably however, the alleles of these SNPs are the alleles representative of *C. melo* subsp. *agrestis* var. *acidulous*.

According to a preferred embodiment of the present invention, the introgressed sequences or interval from *C. melo* subsp. *agrestis* var. *acidulous* present in the genome of a seed or plant of the invention and conferring the resistance to ToLCNDV, are at least 5 kilobases long, and preferably at least 8, 10 or 15 kb long. The introgressed sequences or intervals from *C. melo* subsp. *agrestis* var. *acidulous* are however preferably not too long in order to avoid introgression of non-commercial features associated with the *C. melo* subsp. *agrestis* var. *acidulous* genotype. It is thus preferred according to the invention that the introgressed sequences mentioned above are less than 25 cM in length, preferably less than 20 cM or less than 15 cM. According to more preferred embodiments, the introgressed sequences are less than 10 cM or even less than 5 cM in length and most preferably less than 5 cM in order to avoid or limit linkage drag.

The introgressed sequences are minimized to contain as few as possible sequences unrelated to the desired phenotype.

The seed or plant according to this aspect of the invention is preferably highly resistant to ToLCNDV, inter alia it remains free of symptoms, namely yellowing mosaic, puckering and stunting, till the end of the season when grown under natural infection conditions.

The resistance and/or tolerance according to the invention is mainly a resistance and/or tolerance to ToLCNDV infection, but according to a preferred embodiment, the introgressed sequences also confer resistance to one or more additional geminiviruses, especially resistance to one or more additional begomoviruses.

As detailed above, the invention is directed to *C. melo* subsp. *melo* plants, resistant to ToLCNDV infection, as well as to seeds giving rise to those plants.

A *C. melo* subsp. *melo* plant according to the invention may be a commercial plant or line or variety, preferably cultivated for its fruits. Such a commercial plant or line gives rise to fruits, when grown in suitable conditions and when adequately pollenized, which are marketable. Marketable melon are inter alia characterized by a standard orange flesh color, with possibly patches of cream color, preferably standard orange, and/or a round or oval fruit shape, and/or a brix of at least 9, preferably at least 10. A marketable melon is preferably characterized by the presence of all the features mentioned above, and preferably a round fruit shape, an orange flesh color and a brix of at least 9.

A preferred seed or plant of the invention is thus capable of bearing melons having a standard orange flesh color, as defined in the experimental section. Preferably, such fruits have also a round shape, or round-oval shape. They preferably have a degree brix of at least 9, and preferably at least 10 or 11. The invention also concerns seeds or plants capable of bearing fruits having a brix level higher than 9.

A plant or seed according to the invention may be a progeny or offspring of a plant grown from the deposited seeds of ToLR1, deposited at the NCIMB under the accession number NCIMB 42506. Plants grown from the deposited seeds are indeed homozygously resistant to ToLCNDV, they thus bear in their genome the introgressed sequences from *C. melo* subsp. *agrestis* var. *acidulous* conferring resistance to ToLCNDV, on both homologs of chromosome 11. They can be used to transfer these sequences in another background by crossing and selfing and/or backcrossing.

The introgressed sequences from *C. melo* subsp. *agrestis* var. *acidulous* conferring resistance, or tolerance, to ToLCNDV according to the present invention are homozygoulsy present in the genome of a resistant plant or seed. Accordingly, such a plant exhibits, on both homologs of chromosome 11, introgressed sequences from *C. melo* subsp. *agrestis* var. *acidulous* capable of conferring resistance to ToLCNDV when present homozygously. It must be borne in mind that this thus not necessarily implies that the introgression fragments from *C. melo* subsp. *agrestis* var. *acidulous* on both chromosome 11 homologs are identical. Indeed, one of the homologs may comprise only the introgressed sequences necessary and sufficient to confer resistance, whereas the other homolog comprises a larger introgression fragment, comprising said sequences in addition to further sequences from *C. melo* subsp. *agrestis* var. *acidulous* unrelated to resistance.

The invention is also directed to the deposited seeds ToLR1 (NCIMB 42506) and to plants grown from one of these seeds. These seeds contain homozygously the introgressed sequences conferring the phenotype of interest; they are however distinct on other phenotypic traits such that they do not form a plant variety.

The invention is also directed to resistant plants or seeds as defined above, i.e. containing the introgressed sequences of interest in homozygous form, obtainable by transferring the introgressed sequences from a resistant *C. melo* plant, representative seeds thereof were deposited under NCIMB accession NCIMB-42506, into another *C. melo* subsp. *melo* genetic background, for example by crossing said resistant plant with a second melon plant parent.

In a second aspect, the invention also concerns a second type of plants, seeds or cell, namely plants, seeds or cells of *C. melo* subsp. *melo*, which bear in their genome the introgressed sequences from *C. melo* subsp. *agrestis* var. *acidulous* conferring resistance to ToLCNDV when present homozygously, but which do not bear these sequences on both homologs of chromosome 11; i.e. they are heterozygous for the introgressed sequences conferring the phenotype, namely heterozygous for the resistance locus, or resistance gene. The introgressed sequences of interest are those as defined previously, a copy of which is present in the genome of the deposited seeds, accession number NCIMB 42506.

Due to the fact that the introgressed sequences are present heterozygously in the second type of plants, seeds or cell of the invention, these plants do not exhibit the phenotype of interest, i.e. they are not resistant to ToLCNDV, this trait segregates further to self-pollinations and the phenotype is not expressed when crossing them with other susceptible plants.

According to the invention, said heterozygous plants can be obtained by crossing one homozygous plant mentioned above with a second plant of the *C. melo* subsp. *melo* species, the second plant being susceptible to ToLCNDV and not bearing the introgressed sequences of the invention. For example, a plant according to this embodiment of the invention can be obtained by crossing a plant grown from a seed of ToLR1, deposited at the NCIMB under the accession number NCIMB 42506, with a ToLCNDV-susceptible *C. melo* subsp. *melo* parental line not bearing introgressed sequences from *C. melo* subsp. *agrestis* var. *acidulous*.

Alternatively, said heterozygous plants can also be obtained by crossing an homozyougsly resistant plant according to the 1$^{st}$ aspect of the invention, with a *C. melo* subsp. *melo* plant which is less resistant to ToLCNDV infection than plants of the invention, or which is resistant to ToLCNDV due to another type of resistance, not introgressed from *C. melo* subsp. *agrestis* var. *acidulous*.

The second type of plant according to the invention can of course be obtained by other processes, well known to the skilled reader.

By self-pollinating diploid plants of the 2$^{nd}$ aspect of the invention, the progeny of such a self-pollination will be at 50% also of this type, i.e. bearing the resistance sequences but not displaying the phenotype of interest, at 25% homozygously resistant to ToLCNDV as defined in the first aspect of the invention, and at 25% not resistant and not bearing the resistance sequences from *C. melo* subsp. *agrestis* var. *acidulous*. The ratios may be different if the plant or seed according to the 2$^{nd}$ aspect is not diploid, or if the second parent is also resistant to ToLCNDV, due to another genetic source of resistance.

The invention therefore concerns any hybrid plant of *C. melo* subsp. *melo* likely to be obtained by crossing a plant resistant to ToLCNDV as disclosed in the present description according to the 1$^{st}$ aspect, with a plant of *C. melo* subsp. *melo*, preferably a susceptible one. The hybrid plant can be obtained by crossing either a plant resistant to ToLCNDV according to the invention as female parent and a second plant as male parent, or alternatively by crossing a plant resistant to ToLCNDV according to the invention as male parent and a second plant as female parent.

The presence of the introgressed sequences according to the invention can be revealed by the sequencing of the chromosomal regions of the invention, namely the region delimited by SNP Melon_sbg_617_42 and SNP Melon_sbg_16835_17, more preferably sequencing of the region delimited by Melon_sbg_33761_74 and Melon_sbg_16835_17, and even more preferably sequencing of the region delimited by Melon_sbg_33761_74 and Melon_sbg_22016_36.

Alternatively, the presence of the introgressed sequences can be revealed by identifying alleles of specific SNPs, representative of the introgressed sequences. The presence of the introgressed sequences can thus be tested by testing the presence of one or more of the following alleles: allele T of Melon_sbg_617_42, allele G of Melon_sbg_617_84, allele A of Melon_sbg_20578_63, allele C of Melon_sbg_20578_82, allele A of Melon_sbg_55680_17, allele A of Melon_sbg_60684_74, allele T of Melon_sbg_33761_74, allele G of Melon_sbg_2720_78, allele A of Melon_sbg_14207_58, allele G of Melon_sbg_22016_27, allele G of Melon_sbg_22016_30, allele G of Melon_sbg_22016_36, allele C of Melon_sbg_11556_13, allele C of Melon_sbg_24259_45, allele T of Melon_sbg_16835_5, and allele T of Melon_sbg_16835_17.

Preferably, the presence of the introgressed sequences is revealed by the presence, for one or more of the 10 preferred SNPs of the invention, of the corresponding allele linked to resistance, as defined in table 4, and more preferably by one or more of allele T of Melon_sbg_33761_74, allele G of Melon_sbg_2720_78, allele A of Melon_sbg_14207_58, allele G of Melon_sbg_22016_27, allele G of Melon_sbg_22016_30 and allele G of Melon_sbg_22016_36. The presence of the introgressed sequences is preferably confirmed by testing the presence of at least 2, 3 or 5 of the 16 SNPs of the invention, preferably at least 2, 3, 4 or 5 of the 10 preferred SNPs or of the 6 SNPs Melon_sbg_33761_74, Melon_sbg_2720_78, Melon_sbg_14207_58, Melon_sbg_22016_27, Melon_sbg_22016_30 and Melon_sbg_22016_36.

According to a preferred embodiment, the presence of introgressed sequences of interest is tested by assaying the presence of allele A of Melon_sbg_14207_58, either alone or preferably with allele T of Melon_sbg_33761_74 and/or allele G of SNP Melon_sbg_2720_78.

The heterozygous status of the genome of a plant, seed or plant part with respect to the introgressed sequences of interest can be brought to light by the simultaneous presence of both alleles for the chosen SNP(s), for example by the presence of alleles A and C of SNP Melon_sbg_14207_58.

For all the SNPs of the invention, the alleles linked to resistance and susceptibility are given in table 4.

The presence of the introgressed sequences can also be revealed by genic amplification of sequences in the proximity of the SNPs defined in the present invention, especially Melon_sbg_33761_74, Melon_sbg_2720_78 and Melon_sbg_14207_58, and comparison with the sequence of the respective amplification fragment, obtainable by carrying out the amplification on seeds deposited at the NCIMB under accession number NCIMB 42506, as already mentioned in respect to the 1$^{st}$ aspect.

The invention also concerns any plant likely to be obtained from seed or plants of the invention as described above, and also plant parts of such a plant, and most preferably explant, scion, cutting, seed, fruit, root, rootstock, pollen, ovule, embryo, siliqua, protoplast, leaf, anther, stem, petiole, and any other plants part, wherein said plant, explant, scion, cutting, seed, fruit, root, rootstock, pollen, ovule, embryo, siliqua, protoplast, leaf, anther, stem, petiole, and/or plant part is obtainable from a seed or plant according to the first embodiment of the invention, i.e. bearing the introgressed sequences of interest homozygously in their genome or from a seed or plant according to the second embodiment of the invention, i.e. bearing the introgressed sequences of interest heterozygously in their genome. These plant parts, inter alia explant, scion, cutting, seed, fruit, root, rootstock, pollen, ovule, embryo, siliqua, protoplast, leaf, anther, stem or petiole, comprise in their genome the introgressed sequences from *C. melo* subsp. *agrestis* var. *acidulous* conferring the resistance to ToLCNDV when present homozygously. The introgressed sequences referred to in this aspect of the invention are those defined above in the context of plants of the invention. The different features of the introgressed sequences defined in relation with the first aspect of the invention apply mutatis mutandis to this aspect of the invention. The introgressed sequences are thus preferably chosen from those present in the genome of a plant corresponding to the deposited material ToLR1 (NCIMB accession number 42506). They are advantageously characterized by the presence of allele A for Melon_sbg_14207_58.

The invention is also directed to cells of *C. melo* subsp. *melo* plants, such that these cells comprise, in their genome, introgressed sequences from *C. melo* subsp. *agrestis* var. *acidulous* conferring the phenotype of interest, i.e. resistance and/or tolerance to ToLCNDV when present homozygously. The introgressed sequences are those already defined in the frame of the present invention, they are characterized by the same features and preferred embodiments already disclosed with respect to the plants and seeds according to the preceding embodiments of the invention. The presence of these introgressed sequences can be revealed by the techniques disclosed above and well known to the skilled reader. It can inter alia be determined whether the introgressed sequences are present homozygously or heterozygously in the genome of such a cell of the invention. They are advantageously characterized by the presence of allele A for SNP Melon_sbg_14207_58.

Cells according to the invention can be any type of the *C. melo* subsp. *melo* cell, inter alia a cell capable of regenerating a whole *C. melo* subsp. *melo* plant, bearing introgressed sequences from *C. melo* subsp. *agrestis* var. *acidulous* linked to the phenotype of interest.

The present invention is also directed to a tissue culture of regenerable cells of the plant as defined above according to the present invention; preferably, the regenerable cells are derived from embryos, protoplasts, meristematic cells, callus, pollen, leaves, anthers, stems, petioles, roots, root tips, fruits, seeds, flowers, cotyledons, and/or hypocotyls, and contain in their genome introgressed sequences from *C. melo* subsp. *agrestis* var. *acidulous* on chromosome 11 conferring resistance and/or tolerance to ToLCNDV only when present homozygously.

The tissue culture will preferably be capable of regenerating plants having the physiological and morphological characteristics of the foregoing melon plant, and of regenerating plants having substantially the same genotype as the foregoing melon plant. The present invention also provides melon plants regenerated from the tissue cultures of the invention.

The invention also provides a protoplast of the plant defined above, or from the tissue culture defined above, said protoplast containing the introgressed sequences from *C. melo* subsp. *agrestis* var. *acidulous* conferring resistance to ToLCNDV when present homozygously.

According to a fourth aspect, the present invention is also directed to the use of a melon plant as detailed according to the first aspect of the invention, i.e. resistant, or tolerant depending on the infection conditions, to ToLCNDV, as a breeding partner in a breeding program for obtaining *C. melo* subsp. *melo* plants resistant and/or tolerant to ToLCNDV. Indeed, such a plant according to the first aspect harbors homozygously in its genome introgressed sequences from *C. melo* subsp. *agrestis* var. *acidulous*, conferring the phenotype of interest, i.e. resistance and/or tolerance. By crossing this plant with susceptible or less resistant plants, or with resistant plants bearing another type of ToLCNDV resistance, it is thus possible to transfer these sequences, conferring the desired phenotype, to the progeny as the phenotype is a monogenic trait. A plant according to the invention can thus be used as a breeding partner for introgressing sequences conferring the desired phenotype into a *C. melo* subsp. *melo* plant or germplasm. Although a plant or seed according to the second aspect of the invention, i.e. bearing the introgressed sequences of interest heterozygously, can also be used as a breeding partner as detailed above, the segregation of the phenotype is likely to render the breeding program more complex.

The introgressed sequences from *C. melo* subsp. *agrestis* var. *acidulous* will advantageously be introduced into varieties that contain other desirable genetic traits such as resistance to disease, early fruit maturation, drought tolerance, fruit shape, and the like.

The invention is also directed to the same use with plants or seed of ToLR1, deposited at the NCIMB under the accession number NCIMB 42506. Said plants are also suitable as introgression partners in a breeding program aiming at conferring the desired phenotype to a *C. melo* subsp. *melo* plant or germplasm.

In such a breeding program, the selection of the progeny displaying the desired phenotype, or bearing sequences linked to the desired phenotype, can advantageously be carried out on the basis of the alleles of the SNP markers, especially the SNP markers of the invention. The progeny is preferably selected on the presence of allele A of Melon_sbg_14207_58, allele G of SNP Melon_sbg_2720_78 or allele T of Melon_sbg_33761_74 on chromosome 11. The selection can alternatively be made on the basis of the simultaneous presence of these 3 alleles; or a combination of 2 of these alleles, said combination preferably comprising allele A of Melon_sbg_14207_58.

Alternatively, the other SNPs of the invention can also be used as detailed above, for selection plants or seed having the desired phenotype or bearing introgression sequence conferring said phenotype when present homozygously. According to a preferred embodiment, the selection can advantageously be made on the simultaneous presence of at least 4 or at least 5 of the following SNP alleles: allele T of Melon_sbg_33761_74, allele G of Melon_sbg_2720_78, allele A of Melon_sbg_14207_58, allele G of Melon_sbg_22016_27, allele G of Melon_sbg_22016_30 and allele G of Melon_sbg_22016_36. The presence of these alleles indeed confirms the presence of introgressed sequences at the loci defined by said SNPs; moreover, further to point mutation or recombination event, it is conceivable that at least 1 or 2 of these 6 alleles is lost, the remaining of the introgression fragment however still conferring the phenotype of interest, when present homozygously.

The selection of the progeny having the desired phenotype can also be made on conditions of ToLCNDV infection, as disclosed inter a/ia in example 1 or 2.

According to a preferred embodiment, the phenotype is tested by ToLCNDV mechanical inoculation, as exemplified in example 2, namely by inoculation through rubbing of cotyledons by a solution comprising grinded infected leaves. Such a mechanical inoculation test is particularly suited in breeding program as it is more rapid and easier to carry out than natural infection.

A plant according to the invention, or grown from a seed as deposited under accession number NCIMB 42506, is thus particularly valuable in a marker assisted selection for obtaining commercial melon lines and varieties, resistant or tolerant to ToLCNDV infection.

The invention is also directed to the use of said plants in a program aiming at identifying, sequencing and/or cloning the genes conferring the desired phenotype, i.e. resistance to ToLCNDV.

Any specific embodiment described for the 1$^{st}$, 2$^{nd}$ and 3$^{rd}$ aspects of the invention is also applicable to this aspect of the invention, especially with regard to the features of the introgressed sequences from *C. melo* subsp. *agrestis* var. *acidulous* conferring the resistance when present homozygously.

According to a fifth aspect, the invention also concerns methods or processes for the production of *C. melo* subsp. *melo* plants having the desired phenotype, especially commercial plants. The present invention is indeed also directed to transferring the introgressed sequences conferring the resistance and/or tolerance, to other melon varietie, or other species and is useful for producing new types and varieties of ToLCNDV resistant or tolerant melons.

A method or process for the production of a plant having these features may comprise the following steps:
  a) Crossing a plant corresponding to the deposited seeds (NCIMB 42506), or progeny thereof bearing the sequences conferring the resistance to ToLCNDV, and *C. melo* subsp. *melo* plant, in which the desired phenotype is to be imported or improved; preferably such a *C. melo* subsp. *melo* plant is susceptible or less resistant to ToLCNDV;
  b) Selecting a plant in the progeny thus obtained bearing sequences conferring resistance to ToLCNDV only when present homozygously,
  c) Self-pollinating one or several times the plant obtained at step b) and selecting a resistant plant in the progeny thus obtained;
wherein SNPs markers may be used in steps b) and/or c), for selecting plants bearing sequences conferring resistance to ToLCNDV only when present homozygously and/or plants resistant to ToLCNDV. The SNP markers are preferably one or more of the 16 SNP markers of the invention, and preferably one or more of the 10 preferred SNP markers, more preferably one or more of Melon_sbg_33761_74, Melon_sbg_2720_78, Melon_sbg_14207_58, Melon_sbg_22016_27, Melon_sbg_22016_30 and Melon_sbg_22016_36. According to a preferred embodiment, the selection is at least partly made on the basis of the allele of SNP Melon_sbg_14207_58, with or without use of Melon_sbg_33761_74 and Melon_sbg_2720_78. The selection is even more preferably carried out by detecting the alleles of these 3 SNP markers. Alternatively, the selection can be made on the detection of the allele of at least 2 SNPs chosen amongst the 10 preferred SNPs of the invention, or the 6 SNPs Melon_sbg_33761_74, Melon_sbg_2720_78, Melon_sbg_14207_58, Melon_sbg_22016_27, Melon_sbg_22016_30 and Melon_sbg_22016_36.

Preferably, the selection is made on at least 3 SNPs, preferably at least 4, 5 or 6, one of them being Melon_sbg_14207_58. The selection can also be made on the detection of the alleles of all these SNPs.

According to a preferred embodiment, the selection is made on the basis of the alleles of the 3 SNPs Melon_sbg_33761_74, Melon_sbg_2720_78 and Melon_sbg_14207_58.

In order to identify plants bearing homozygously the introgressed sequences responsible for the resistance to ToLCNDV, the presence of the allele linked to the resistance is to be detected in combination with the absence of the allele linked to the recurrent parent.

In order to identify plants bearing heterozygously the introgressed sequences, the sole presence of the allele linked to the resistance is to be detected.

Preferably, the *C. melo* subsp. *melo* plant of step a) is an elite line, used in order to introduce commercially desired traits or desired horticultural traits.

A method or process as defined above may advantageously comprises backcrossing steps, preferably after step c), in order to obtain plants having all the characterizing features of *C. melo* subsp. *melo* plants. Consequently, a method or process for the production of a plant having these features may also comprise the following additional steps:
  d) Backcrossing the resistant plant selected in step c) with a *C. melo* subsp. *melo* plant;
  e) Selecting a plant in the progeny bearing sequences conferring resistance to ToLCNDV only when present homozygously,
  f) Self-pollinating the plant obtained at step e) or crossing distinct plants obtained at step e), and
  g) Selecting a plant resistant to ToLCNDV.

The plant used in step a), namely the plant corresponding to the deposited seeds can be a plant grown from the deposited seeds, or progeny thereof bearing the sequences conferring the resistance to ToLCNDV; it may alternatively be any plant according to the 1$^{st}$ aspect of the invention, i.e. homozygously resistant to ToLCNDV.

Alternatively, the method or process may comprise the following steps:
  a1) Crossing a plant corresponding to the deposited seeds (NCIMB 42506), or progeny thereof bearing the sequences conferring the resistance to ToLCNDV, and a *C. melo* subsp. *melo* plant, in which the desired phenotype is to be imported or improved, thus generating the F1 population;
  a2) Advancing the F1 population to create F2 population;
  b) Selecting resistant individuals in the progeny thus obtained;

c) Optionally self-pollinating one or several times the resistant plant obtained at step b) and selecting a resistant plant in the progeny thus obtained;
d) Optionally backcrossing the resistant plant selected in step b) or c) with a *C. melo* subsp. *melo* plant,
e) Selecting in the progeny a plant bearing sequences linked to the desired phenotype,
f) Self-pollinating the plant obtained at step e) or crossing distinct plants obtained at step e), one or several times, and
g) selecting a plant resistant to ToLCNDV.

The *C. melo* subsp. *melo* plant of steps a) or a1) and d) can be any *C. melo* subsp. *melo* plant but preferably a susceptible plant or less resistant than the plants of the invention.

The plant selected at step b), c) or g) of the preceding methods may be a commercial plant, especially a plant having fruits which have a round or round-oval shape, an orange flesh color_ with possibly patches of cream color_ and/or a brix of at least 9, at full maturity in normal culture conditions.

Steps d), e) and/or f) may be repeated twice or three times or more, not necessarily with the same *C. melo* subsp. *melo* plant. Said *C. melo* subsp. *melo* plant is preferably a breeding line. This plant is preferably an elite line, used in order to introduce commercially desired traits or desired horticultural traits.

The self-pollination/crossing and backcrossing steps may be carried out in any order and can be intercalated, for example a backcross can be carried out before and after one or several self-pollinations/crossings, and self-pollinations/crossings can be envisaged before and after one or several backcrosses.

Moreover, the methods of the invention are advantageously carried out by using SNP markers for one or more of the selection steps for selecting plants bearing the introgressed sequences linked to the ToLCNDV resistance and/or tolerance, or for selecting plants having the phenotype of interest.

The SNP markers are preferably one or more of the 10 preferred SNPs, preferably Melon_sbg_33761_74, Melon_sbg_2720_78, Melon_sbg_14207_58, Melon_sbg_22016_27, Melon_sbg_22016_30 and Melon_sbg_22016_36, and even more preferably Melon_sbg_14207_58. According to a preferred embodiment, the selection is at least partially made on the basis of the allele of Melon_sbg_14207_58. All these preferred embodiments have already been detailed in the context of the present invention and are identical for this aspect. In order to identify plants bearing homozygously the introgressed sequences responsible for the resistance to ToLCNDV, the presence of the allele linked to the resistance, for the SNPs of the invention, is to be detected in combination with the absence of the allele linked to the recurrent susceptible parent.

Preferably, the selection of a resistant plant is carried out by the detection of:
the presence of allele T of SNP Melon_sbg_33761_74 combined with the absence of allele C for said SNP; and/or
the presence of allele G of SNP Melon_sbg_2720_78 combined with the absence of allele A for said SNP; and/or
the presence of allele A of SNP Melon_sbg_14207_58 combined with the absence of allele C for said SNP; and/or
the presence of allele G of SNP Melon_sbg_22016_27 combined with the absence of allele C for said SNP; and/or
the presence of allele G of SNP Melon_sbg_22016_30 combined with the absence of allele A for said SNP; and/or
the presence of allele G of SNP Melon_sbg_22016_36 combined with the absence of allele A for said SNP.

The selection of the progeny having the desired phenotype can also be made on conditions of ToLCNDV infection, as disclosed inter alia in example 1 of mechanical inoculation, as described in example 2.

The method used for allele detection can be based on any technique allowing the distinction between two different alleles of a SNP, on a specific chromosome locus.

The present invention also concerns any breeding scheme involving as first step crossing a plant grown from one of the deposited seeds (NCIMB 42506).

The present invention also concerns a plant obtained or obtainable by one of the methods described above. Such a plant is indeed a *C. melo* subsp. *melo* plant having the desired phenotype according to the first aspect of the invention, i.e. resistant and/or tolerant to ToLCNDV.

The invention also provides a method for producing a hybrid *C. melo* subsp. *melo* seed comprising crossing a first cultivar plant parent with a second cultivar plant parent and harvesting the resultant hybrid *C. melo* subsp. *melo* seed, wherein both parents are cultivars containing the introgressed sequences in the homozygous state. The hybrid seeds, plant and parts thereof produced by such method are also part of the invention.

The invention is moreover directed to a method for detecting and/or selecting *C. melo* subsp. *melo* plants having introgressed sequences from *C. melo* subsp. *agrestis* var. *acidulous* conferring resistance and/or tolerance to ToLCNDV when present homozygously, on the basis of the allele detection of at least one SNP chosen amongst the 10 preferred SNPs of the invention on chromosome 11, and more preferably the 6 SNPs Melon_sbg_33761_74, Melon_sbg_2720_78, Melon_sbg_14207_58, Melon_sbg_22016_27, Melon_sbg_22016_30 and Melon_sbg_22016_36. The method may be carried out on *C. melo* subsp. *melo* plants resistant to ToLCNDV; the method thus can be used to confirm that such plants comprise in their genome the introgressed sequences from *C. melo* subsp. *agrestis* var. *acidulous* according to this invention, and thus have been obtained according to the present invention.

Preferably, plants bearing the introgressed sequences are selected if at least one of the following markers, and preferably at least 2, 3, 4, 5 or all, of allele T of Melon_sbg_33761_74, allele G of Melon_sbg_2720_78, allele A of Melon_sbg_14207_58, allele G of Melon_ sbg_22016_27, allele G of Melon_sbg_22016_30 and allele G of Melon_sbg_22016_36, is/are detected, in a genetic material sample of the plant to be selected. More preferably, a plant is selected if at least one, two or all of the following alleles is/are detected: allele A of Melon_sbg_14207_58, allele G of Melon_sbg_2720_78 and allele T of Melon_sbg_33761_74. According to a preferred embodiment, the allele of interest which is detected is present homozygously in the selected plant, i.e. no other allele of said SNP is present. In such a case, it can be concluded that the plant bears the introgressed sequences and is resistant to ToLCNDV. Preferred detection methods are detailed above and applicable to this aspect of the invention.

According to a particularly preferred embodiment, the selection is made on the presence of allele A of Melon_sbg_14207_58. For selection of plants displaying the phenotype of resistance and/or tolerance to ToLCNDV, the selection is preferably made on the detection of allele A of Melon_sbg_14207_58 in combination with no detection of any other allele for this SNP, and especially no detection of allele C.

In addition to introgression of the sequences conferring resistance (or tolerance, depending on the infection conditions) to ToLCNDV infections by crossing, as detailed in the methods of the invention, these sequences of the invention can also be introduced into *C. melo* subsp. *melo* background by genetic engineering in order to obtain a commercial *C. melo* subsp. *melo* plant resistant to ToLCNDV. The identification and cloning of the introgressed sequences from *C. melo* subsp. *agrestis* var. *acidulous* conferring the desired phenotype, inter alia from the deposit NCIMB 42506, can be carried out by the skilled person, on the basis of the sequence information given in the present application and deposited material.

According to a further aspect, the present invention is also directed to hybrid plants of *C. melo* subsp. *melo* obtainable by crossing a resistant plant according to the first aspect of the invention, or a resistant plant obtainable by the methods disclosed above, with a plant of *C. melo* subsp. *melo*, for example a plant susceptible to ToLCNDV infection, or a plant with a different level of resistance to ToLCNDV infection.

A particularly preferred hybrid *C. melo* subsp. *melo* plant, is a plant which displays any trait or phenotype of agronomical interest.

LEGEND OF FIGURES

Figure 3:
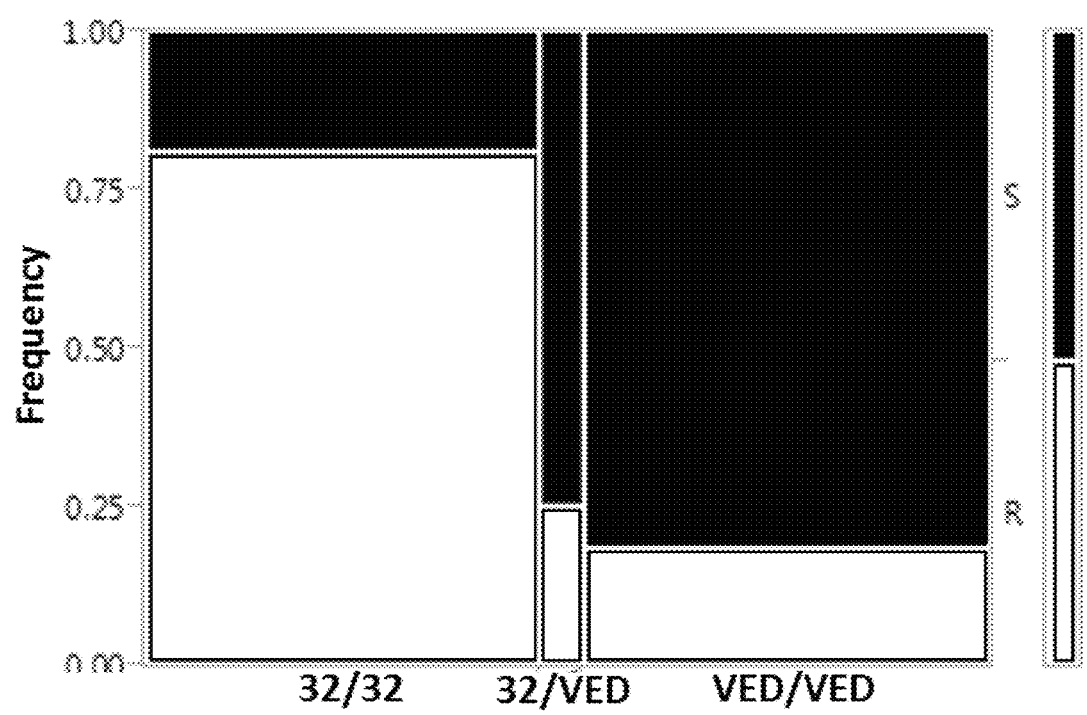

FIG. 3 is a mosaic plot showing frequencies of phenotypes for each genotypic group determined by "Melon_sbg_14207_58". Over all this SNP predicts the phenotype of 81% from RIL. R (resistant) and S (susceptible) proportions are denoted by white and black colors, respectively.

EXAMPLES

Example 1: ToLCNDV Insect Mediated Inoculation and Disease Screening

Tomato leaf curl New Delhi virus (ToLCNDV) is caused by a whitefly transmitted geminivirus. The identification of source of resistance involves the development of a phenotyping system based on the four following aspects that have to be validated for repeatability and reliability:
the virus growth and maintenance,
the vector growth and maintenance,
the inoculation
and the scoring methodologies.
Virus Growth and Maintenance
The Tomato leaf curl New Delhi virus (ToLCNDV) was maintained on isolated infected squash plants (*Cucurbita pepo*) grown in an insect-proof cages, with natural lighting and temperature control (25° C. during the day and 20° C. during the night). Cultures of the ToLCNDV were maintained on susceptible squash plants (*Cucurbita pepo*) 'Victoria F1" (HM.Clause) (thus confirming that the ToLCNDV is indeed a strain, giving rise to the severe symptoms described above).

It must be noted that the presence of ToLCNDV was confirmed using PCR as described in Ruiz et al. 2015 and the absence of CVYV and CYSDV confirmed according to Ruiz et al. 2006.

Whitefly Maintenance

Whitefly (*Bemisia tabaci*, biotype B) colonies were reared on eggplant (*Solanum melongena* L.) plants grown in muslin-covered cages maintained inside an insect-proof greenhouse with natural lighting and temperature control (25° C. during the day and 20° C. during the night). Adult whiteflies were provided with a 48-h acquisition access period on ToLCNDV infected squash plants (*Cucurbita pepo*) 'Victoria F1.

Inoculation of Plants

The acquisition access period was followed by a 72-h inoculation access period on the melon (*Cucumis melo*) plants to be tested for resistance to ToLCNDV, said plants being at the one true leaf development level. The plant infestation was effective as at least 10 whiteflies per *melo* plant were observed. Following the inoculation access period, the whiteflies were removed by treating plants with imidacloprid (Confidor; Bayer, Leverkusen, Germany). The plants were transplanted in the greenhouse (insect-proof greenhouse with natural lighting and temperature control (30° C. during the day and 25° C. during the night), during spring and late summer/fall seasons (April and August, respectively), for a six weeks incubation period.

Disease Screening

The development of symptoms (leaves in upper part of plant showing yellowing mosaic, puckering and stunting of the plants) was followed and registered 45 days post inoculation (DPI) using three levels, namely resistant (no symptom), intermediate (moderate yellowing mosaic) or susceptible (symptomatic, with strong yellow mosaic, puckering and stunting).

Example 2: ToLCNDV Mechanical Inoculation

In addition to the insect mediated inoculation described in example 1, the present inventors also developed an artificial test based on mechanical inoculation. Naturally squash plants infected with ToLCNDV were collected in Almeria and the virus was isolated. Infected leaves were kept in a plastic bag at −80° C. up to their use. 1 g of infected leaves is grinded with 4 ml of a 0.03M Na2HPO4 buffer (pH9) containing 0.2% sodium diethyldithiocarbamate with carborundum (7.5%) and activated carbon (10%). Seedlings with first leaf not yet emerged are inoculated on both cotyledons by gentle rubbing and plants are rinsed after inoculation. Plants are then maintained in growth chamber with a day temperature of 25° C. for 14 hours and a night temperature of 20° C. for 10 hours. A second inoculation can be performed one week after the initial one in order to insure infection.

A first scoring is done 3 weeks after inoculation, when the susceptible check show clear symptoms, a second one being done one week later to confirm the reactions. The rating is on a 1 to 9 scale where 1 is for plants having severe symptoms (leaf cupping, plant stunting); 3 is for plants with obvious symptoms such as vein banding or vein clearing, and beginning of lead cupping, 5 if for plants having mild symptoms such as yellow mosaic, 7 is for plants having only slight symptoms, i.e. light yellowing or light leaf curling and 9 is for symptomless plants.

Example 3: Identification of a Source of Resistance to ToLCNDV Through Insect Mediated Inoculation As a starting point of the realization of the invention, the present inventors have conducted several experiments to screen for ToLCNDV resistance among several *Cucumis melo* plants, both from *Cucumis melo* subsp. *agrestis* and from *Cucumis melo* subsp. *melo*. It must be noted that, to date, *Cucumis melo* subsp. *agrestis* var. *acidulous* has not been identified as a possible source of resistance to ToLCNDV.

A panel of 27 commercial *Cucumis melo* subsp. *melo* hybrids as well as 8 *Cucumis melo* subsp. *agrestis* and *Cucumis melo* subsp. *melo* were screened according to the process described in Example 1. A susceptible check was added as control.

TABLE 1

| | Plants tested for resistance | | | |
|---|---|---|---|---|
| Plant identifier and type of plants tested | Nb of Resistant plants | Nb of Intermediate plants | Nb of Susceptible plants | Total Plant nb |
| H-MLCND-1: *C. melo* subsp. *melo* var. *cantalupensis* Galia | 0 | 0 | 10 | 10 |
| H-MLCND-2: *C. melo* subsp. *melo* var. *cantalupensis* Galia | 0 | 0 | 5 | 5 |
| H-MLCND-3: *C. melo* subsp. *melo* var. *cantalupensis* Galia | 0 | 0 | 10 | 10 |
| H-MLCND-4: *C. melo* subsp. *melo* var. *cantalupensis* Galia | 0 | 0 | 10 | 10 |
| H-MLCND-5: *C. melo* subsp. *melo* var. *cantalupensis* Galia | 0 | 0 | 5 | 5 |
| H-MLCND-6: *C. melo* subsp. *melo* var. *cantalupensis* Galia | 0 | 0 | 10 | 10 |
| H-MLCND-7: *C. melo* subsp. *melo* var. *cantalupensis* Galia | 0 | 0 | 10 | 10 |
| H-MLCND-8: *C. melo* subsp. *melo* var. *cantalupensis* Galia | 0 | 0 | 10 | 10 |
| H-MLCND-9: *C. melo* subsp. *melo* var. *cantalupensis* Galia | 0 | 0 | 5 | 5 |
| H-MLCND-10: *C. melo* subsp. *melo* var. *cantalupensis* Galia | 0 | 0 | 7 | 7 |
| H-MLCND-11: *C. melo* subsp. *melo* var. *cantalupensis* Galia | 0 | 0 | 7 | 7 |
| H-MLCND-12: *C. melo* subsp. *melo* var. *cantalupensis* Galia | 0 | 0 | 10 | 10 |
| H-MLCND-13: *C. melo* subsp. *melo* var. *cantalupensis* Galia | 0 | 0 | 10 | 10 |
| H-MLCND-14: *C. melo* subsp. *melo* var. *cantalupensis* Galia | 0 | 3 | 6 | 9 |
| H-MLCND-15: *C. melo* subsp. *melo* var. *cantalupensis* Galia | 0 | 0 | 10 | 10 |
| H-MLCND-16: *C. melo* subsp. *melo* var. *cantalupensis* Galia | 0 | 0 | 8 | 8 |
| H-MLCND-17: *C. melo* subsp. *melo* var. *cantalupensis* Galia | 0 | 0 | 8 | 8 |
| H-MLCND-18: *C. melo* subsp. *melo* var. *cantalupensis* Galia | 0 | 0 | 8 | 8 |
| H-MLCND-19: *C. melo* subsp. *melo* var. *cantalupensis* Galia | 0 | 0 | 5 | 5 |
| H-MLCND-20: *C. melo* subsp. *melo* var. *cantalupensis* Galia | 0 | 0 | 10 | 10 |
| H-MLCND-21: *C. melo* subsp. *melo* var. *cantalupensis* Galia | 0 | 0 | 10 | 10 |
| H-MLCND-22: *C. melo* subsp. *melo* var. *cantalupensis* Galia | 0 | 0 | 10 | 10 |
| H-MLCND-23: *C. melo* subsp. *melo* var. *cantalupensis* Galia | 0 | 1 | 9 | 10 |
| H-MLCND-24: *C. melo* subsp. *melo* var. *cantalupensis* Galia | 0 | 0 | 10 | 10 |
| H-MLCND-25: *C. melo* subsp. *melo* var. *cantalupensis* Galia | 0 | 0 | 10 | 10 |
| H-MLCND-26: *C. melo* subsp. *melo* var. *cantalupensis* Galia | 0 | 0 | 10 | 10 |
| H-MLCND-27: *C. melo* subsp. *melo* var. *ameri ananas* | 0 | 0 | 10 | 10 |
| H-MLCND-28: *C. melo* subsp. *melo* var. *ameri ananas* | 0 | 0 | 10 | 10 |
| H-MLCND-31: *C. melo* subsp. *agrestis* var. *chinemsis* | 0 | 7 | 2 | 9 |
| H-MLCND-32: *C. melo* subsp. *agrestis* var. *acidulous* | 4 | 2 | 1 | 7 |

TABLE 1-continued

| | Plants tested for resistance | | | |
|---|---|---|---|---|
| Plant identifier and type of plants tested | Nb of Resistant plants | Nb of Intermediate plants | Nb of Susceptible plants | Total Plant nb |
| H-MLCND-33: Not defined | 0 | 6 | 0 | 6 |
| H-MLCND-34: Not defined | 0 | 0 | 10 | 10 |
| H-MLCND-35: Not defined | 4 | 5 | 1 | 10 |
| H-MLCND-36: Not defined | 0 | 7 | 0 | 7 |

Two resistant leads were identified, namely H-MLCND-32 and H-MLCND-35. Lead H-MLCND-32 was chosen by the present inventors as a possible source of resistance to ToLCNDV. It is a *Cucumis melo* subsp. *agrestis* var. *acidulous*, with white green, firm and crisp flesh with low sugar content (a brix level of 5.5) and no aroma, all such characteristics that would render any melon fruit unmarketable.

Example 4: Phenotyping of a RIL Mapping Population

For a genetic mapping experiment, 82 Recombinant Inbred Lines (RIL) were selected. These are F6-F8 lines developed by Single Seed Descent from a cross between *C. melo* subsp *agrestis* var. *acidulous* H-MLCND-32, with a susceptible line *C. melo* subsp. *melo* Vedrantais. All lines were infected as described in the example 1 and then transplanted in the greenhouse and screened for resistance against the ToLCNDV according to the disease screening notation described in example 1. It is to be noted that none of tested plants were scored as 'intermediate'. The experiment was conducted in complete blocks design with 4 replicates of single plants. In addition, one block with un-infected plants were grown in the greenhouse to enable comparison between infected and non-infected plants of each line.

TABLE 2 level of resistance of the 82 RILs and of the 2 recurrent parents.

| RIL | Phenotype | RIL | Phenotype | RIL | Phenotype | RIL | Phenotype |
|---|---|---|---|---|---|---|---|
| RIL-1 | R | RIL-2 | S | RIL-3 | S | RIL-4 | S |
| RIL-5 | S | RIL-6 | S | RIL-7 | R | RIL-8 | S |
| RIL-9 | R | RIL-10 | S | RIL-11 | S | RIL-12 | R |
| RIL-13 | R | RIL-14 | S | RIL-15 | S | RIL-16 | R |
| RIL-17 | S | RIL-18 | R | RIL-19 | R | RIL-20 | S |
| RIL-21 | S | RIL-22 | R | RIL-23 | S | RIL-24 | S |
| RIL-25 | S | RIL-26 | R | RIL-27 | S | RIL-28 | R |
| RIL-29 | R | RIL-30 | R | RIL-31 | S | RIL-32 | S |
| RIL-33 | R | RIL-34 | R | RIL-35 | R | RIL-36 | S |
| RIL-37 | S | RIL-38 | S | RIL-39 | R | RIL-40 | R |
| RIL-41 | R | RIL-42 | S | RIL-43 | R | RIL-44 | R |
| RIL-45 | S | RIL-46 | S | RIL-47 | R | RIL-48 | R |
| RIL-49 | S | RIL-50 | R | RIL-51 | S | RIL-52 | R |
| RIL-53 | S | RIL-54 | S | RIL-55 | S | RIL-56 | R |
| RIL-57 | R | RIL-58 | S | RIL-59 | R | RIL-60 | S |
| RIL-61 | S | RIL-62 | R | RIL-63 | R | RIL-64 | S |
| RIL-65 | R | RIL-66 | R | RIL-67 | S | RIL-68 | R |
| RIL-69 | R | RIL-70 | S | RIL-71 | S | RIL-72 | S |
| RIL-73 | R | RIL-74 | R | RIL-75 | R | RIL-76 | S |
| RIL-77 | S | RIL-78 | R | RIL-79 | R | RIL-80 | S |
| RIL-81 | S | RIL-82 | R | HMLCND-32 | R | Vendrantais | S |

R stands for resistant, S stands for susceptible.

Example 5: Confirmation of the Resistance

A plant derived from the same C. melo subsp. agrestis var. acidulous H-MLCND-32 was used in a ToLCNDV mechanical inoculation pathology test according to example 2 and resulted in the confirmation of the resistance.

Example 6: Genetic Determinism of the Resistance

A test was performed to identify the genetic determinism of the resistance identified in C. melo subsp. agrestis var. acidulous H-MLCND-32: The plant of example 5 was crossed with a susceptible melon proprietary line and the F1 progenies plants thereof were inoculated and scored according to the protocol of example 2, whereby scoring of 1 or 3 will be considered as susceptible plants, 5 would be intermediate resistance plants having mild symptoms and 7 and 9 would be for resistant plants. The resistance was preliminary identified as a recessive resistance as all F1 plants scored susceptible.

The scoring was repeated on F2 plants that confirmed the preliminary identification as a monogenic recessive inheritance of the resistance (¼ of resistant plants and ¾ of susceptible ones).

TABLE 3 scoring of F2 plants.

| Plant | Nb of plants | R | IR | S | Observed ratio | Expected ratio | p-value |
|---|---|---|---|---|---|---|---|
| Susceptible control | 26 | 0 | 0 | 26 | 0:26 | 0:26 | |
| Susceptible parent | 10 | 0 | 0 | 10 | 0:10 | 0:10 | |
| Resistant parent | 10 | 9 | 1 | 0 | 9:1 | 1:0 | 0.3049 |
| F1 plant | 10 | 0 | 0 | 10 | 0:10 | 0:10 | |
| F2 plant | 206 | 39 | 9 | 158 | 39:167 | 52:154 | 0.1226 |

R = resistant;
S = susceptible,
IR = intermediate resistant

Each plant was scored and analyses were done using JMP software (SAS) (statistical software). Those qualitative data were analyzed according non parametric statistic tests ($Khi^2$). The p value shows that the differences between the expected ratio and the observed ratio for a recessive gene are not significatively different, from a statistical point of view.

Example 7: Development of Genetic Data and Molecular Markers

SNP Genotyping (Sequence-Based Genotyping)

The sequencing procedure was started with an in silico analysis to select the best Primer Combination (PC), i.e. to choose a PC that generates the least fragments in organelles. Next, DNA of RILs and the two parents were used to generate one library based on the High Throughput AFLP-based polymorphism detection method developed by Keygene (see WO2007/073165 and WO2008/007951). In the present case, the DNA was digested by EcoRI and MseI and adapters were added. These adapters further contain selective bases allowing to reduce the genome to be sequenced. Accordingly to the nomenclature described by Keygene, the library is an EcoRI/MseI+0/+2, meaning that no selective base was added to the 3' end of the primer complementary to the restriction site made by the EcoRI digestion while 2 selective bases have been added to the 3' end of the primer complementary to the restriction site made by the MseI. The library was prepared for Illumina single-end sequencing on the HiSeq system. This library was used for SNP discovery and genotyping. Illumina reads were filtered on quality, presence of sample identification tags and the restriction site motif. From the remaining reads, sample identification tags were removed. Secondly a reference was created: reads from all samples that passed the pre-processing were combined and grouped. Ideally, each cluster represents a single restriction fragment and each restriction fragment is represented by a single cluster. A single sequence was selected from each cluster as representative of the corresponding restriction fragment. Together, these sequences form the reference set. Subsequently filtered reads were mapped to the reference using the 'BWA software' and genotyped for SNPs using the GATK UnifiedGenotyper software. Further information on Sequence-Based Genotyping as well as kits for performing such processes, such as for example the SBG 100-Kit can be ordered from Keygene B.V.

Identifying Markers Significantly Linked to Resistance to ToLCNDV

Phenotypic data: Phenotypic data was collected as described in example 4.

Linkage analysis: The genotyping information described in the SNP genotyping section and the phenotypic measurements were used as input to linkage analysis via Chi-Square test, (JMP), i.e., for each marker the frequencies of resistant and susceptible lines were compared between genotypic groups.

Results

Figure 1:
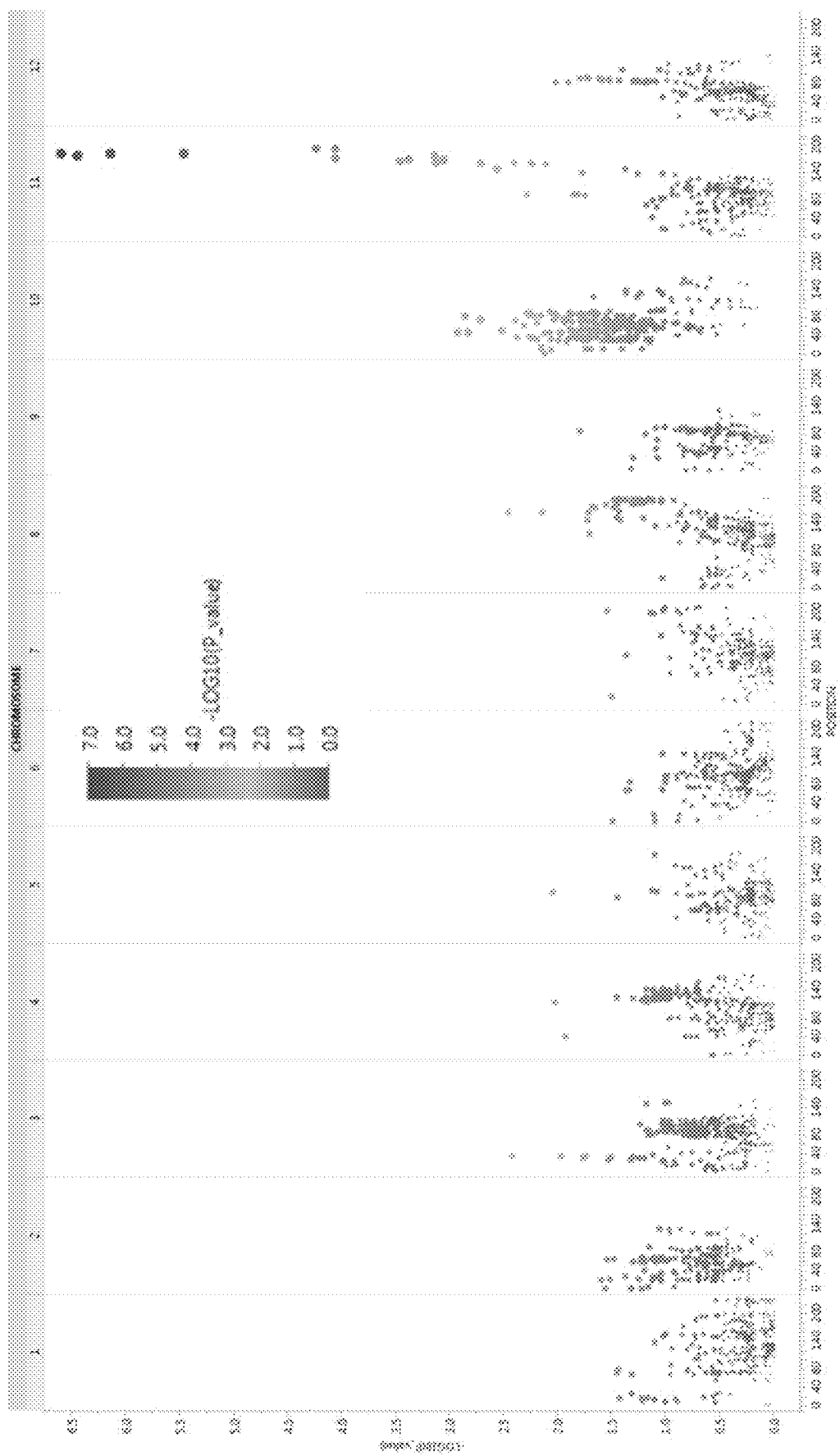
FIG. 1 is the Manhattan plot showing mapping results of RIL population. Vertical axis (y-axis) shows the −log 10 (p-value) and horizontal axis (x-axis) represents all SNPs by their positions (in centimorgan CM) by chromosomes along the genetic map.
Figure 2:
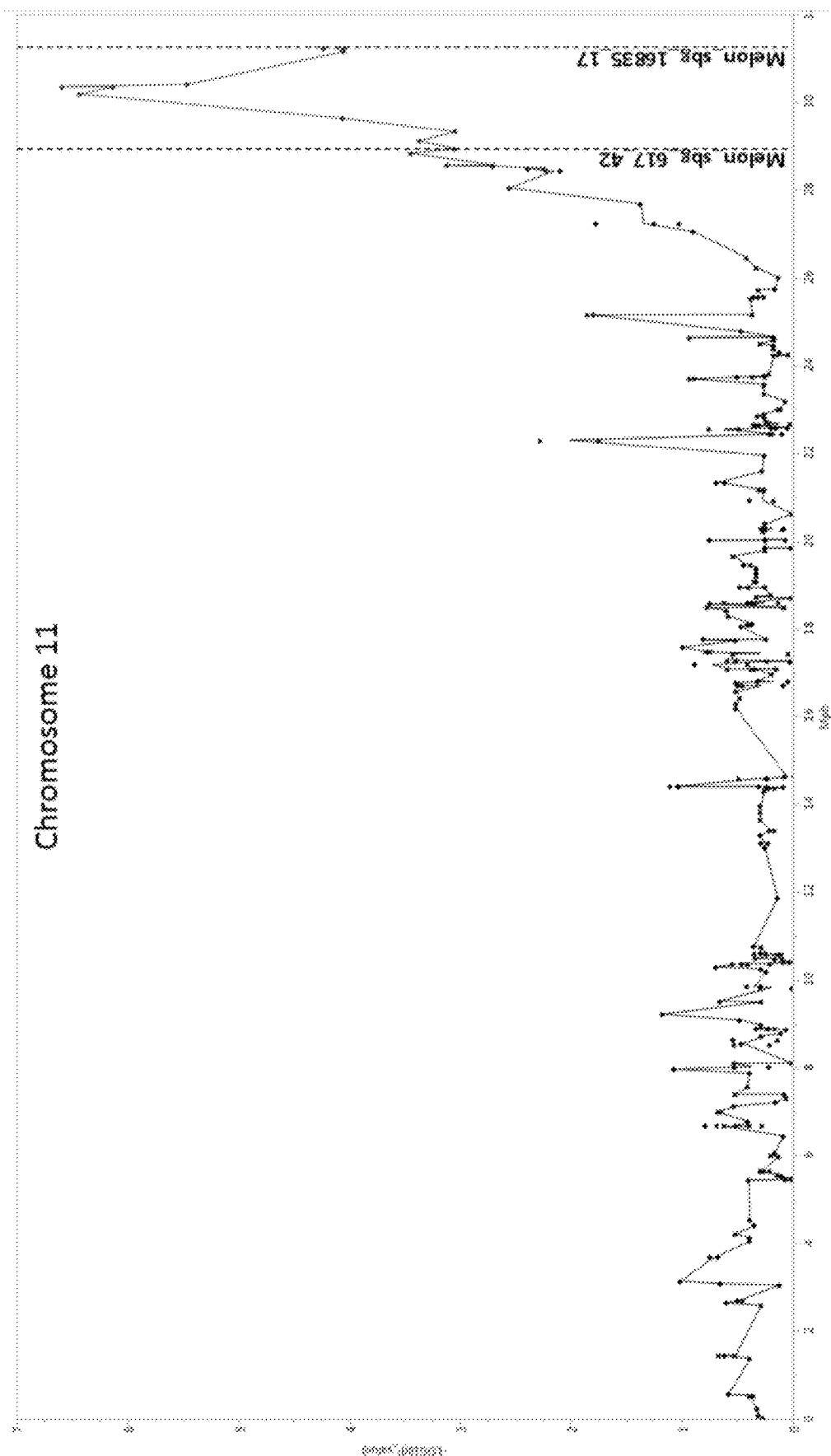
FIG. 2 illustrates a zooming of FIG. 1 in chromosome 11. Vertical axis shows −log 10 (p-value) and horizontal axis represent all SNPs by their position (Mbp) as mapped on the Melon genome.

Linkage analysis identified a single major QTL on chromosome 11 which is defined by set of markers significantly linked to resistance to ToLCNDV. FIG. 1 showing the mapping results of the RIL population illustrates this point. FIG. 2, specific for chromosome 11, illustrates the specific portion of chromosome 11 bearing this major QTL.

The list of associated markers and their significance are summarized in table 4. The SNPs were physically mapped to the public available melon genomic map (https://melonomics.net/files/Genome/Melon_genome_v3.5.1/).

Example 8: Definition of the Introgressed Fragment Conferring Resistance Unlinked to Unmarketable Characteristics The p-value obtained for each SNP marker, and the phenotype of the different RIL harboring the SNP marker allele linked to the resistance, have been taken into consideration in order to define the introgressed fragment, conferring the resistance to ToLCNDV when present homozygously without conferring unmarketable characteristics. The three lines RIL-30, RIL-69 and RIL-82, having fruits displaying the phenotype of marketable melons have been retained. Their genotype with respect to the SNP identified in the previous examples is reported in table 5.

TABLE 4

SNPs linked to ToLCNDV resistance, location and flanking sequences:
Loc: Location on chromosome 11-Nt R: Nucleotide in resistant bulk, corresponding to alleles of H-MLCND-32. Nt S: Nucleotide in susceptible bulk. It must be borne in mind that, outside the introgression fragment of the invention, delimited by SNP Melon_sbg_617_42 and Melon_sbg_16835_17, preferably by Melon_sbg_33761_74 and Melon_sbg_22016_36, the association with susceptible/resistance phenotype is very low.

| SNP | Sequence surrounding the SNP | Left border | Right border | SNP position | P-Value | Nt R | Nt S | Seq ID |
|---|---|---|---|---|---|---|---|---|
| Melon_sbg_2869_86 | TCACGCCGTGTTTCAACGCACAAATTGAATTTCCGACACCCTTATATTATTATCACCTCCACTCCCCCACCCGCCGCCCTCTC[C/T]CGC | 28,024,900 | 28,024,988 | 28,024,985 | 0.002715 | T/T | C/C | 17 |
| Melon_sbg_3859_5 | ACCG[G/T]CGACTCATTGGTCCGGCCACAGAGGAGAGAGAGAGATTGATGCTCAAGCGTGCGAGCATGCCAGGGGAAGGGGTTCGCACGC | 28,404,869 | 28,404,957 | 28,404,873 | 0.005816 | T/T | G/G | 18 |
| Melon_sbg_21303_5 | ACCG[G/T]CGACTCATTGGTCCGGCCACAGAGGAGAGAGAGAGATTGATGCTCAAGCGTGCGAGCATGCCGAGGGGAAGGGGTTCGCACGCGC | 28,404,869 | 28,404,959 | 28,404,873 | 0.007771 | T/T | G/G | 19 |
| Melon_sbg_15226_34 | GAGGCAGTCTTCTCCCCATGTAGACTTCATTCT[T/A]CCCGTGGAATAGATCGAATACGTAACCGATGATCCCGCCGGAACGAAGGTTCCGT | 28,468,747 | 28,468,835 | 28,468,780 | 0.003917 | A/A | A/A | 20 |
| Melon_sbg_40291_40 | GCACCCGAATGATCTTCAAGACGTGTTGTTACGTCTTAC[T/A]TTTGATAATATTTGTGGTTTGGCTTTTGGAAAGATCCAATGACTTGTG | 28,469,424 | 28,469,512 | 28,469,463 | 0.005557 | A/A | T/T | 21 |
| Melon_sbg_8091_11 | ACCGGGGCGG[C/T]GCTTTCAGGACGTTGAAGGAAAATGAATGGACCAAACGAGAACGACCAAAGTTGGGTCGACGTCCAAATCAGCATTTC | 28,524,917 | 28,525,005 | 28,524,927 | 0.001933 | C/C | T/T | 22 |
| Melon_sbg_29917_65 | GGAGCAATGCGACGACGCCGTCACCGTCTGACGTGGAGGAGTTGGATTATGTGGAAGACGATGA[C/G]GACGATGAGGAGGAGGAGGACGGC | 28,541,411 | 28,541,499 | 28,541,475 | 0.000741 | G/G | C/C | 23 |
| Melon_sbg_1548_24 | CACGCTGCATTCCTAGCACCAT[T/A]GGCCAAATGTCTAACCTCAACCAAATTCTCTTTCTCGGCAACAAGCTCGGTGGTTGTTTCCACC | 28,547,660 | 28,547,748 | 28,547,683 | 0.001933 | T/T | A/A | 24 |
| Melon_sbg_22966_49 | TTGTTTGGAGAGTCTGGCTTGCGGCGTTCCAACCGTGGGCGTTTCCACA[G/A]TGGTCCGATCAAGCGACCAACACTAAGACATTCAGGACT | 28,815,310 | 28,815,398 | 28,815,381 | 0.000347 | A/A | G/G | 25 |
| Melon_sbg_22966_72 | TTGTTTGGAGAGTCTGGCTTGCGGCGTTCCAACCGTGGCGTTTCCACAGTGGTCCGATCAAGCGACCAACA[C/G]TAAGACATTCAGGACT | 28,815,310 | 28,815,398 | 28,815,358 | 0.000347 | G/G | C/C | 26 |
| Melon_sbg_ | AACCAAAGTACCTGTTGGGGCTCTTTCCCGT | 28,922,005 | 28,922,093 | 28,922,046 | 0.000867 | T/T | G/G | 1 |

TABLE 4-continued

SNPs linked to ToLCNDV resistance, location and flanking sequences:
Loc: Location on chromosome 11-Nt R: Nucleotide in resistant bulk, corresponding to alleles of H-MLCND-32. Nt S: Nucleotide in susceptible bulk. It must be borne in mind that, outside the introgression fragment of the invention, delimited by SNP Melon_sbg_617_42 and Melon_sbg_16835_17, preferably by Melon_sbg_33761_74 and Melon_sbg_22016_36, the association with susceptible/resistance phenotype is very low.

| SNP | Sequence surrounding the SNP | Left border | Right border | SNP position | P-Value | Nt R | Nt S | Seq ID |
|---|---|---|---|---|---|---|---|---|
| 617_42 | CAATCCGGTC[G/T]GGCTCCGCATGTGCCACAGCTACAATGTGGCGTCTGGCCAAACCGGT | | | | | | | |
| Melon_sbg_617_84 | AACCAAAGTACCTGTTGGGGCTCTTTCCCGTCAATCCGGTCGGGCTCCGCATGTGCCACAGCTACAATGTGGCGTCTGGCCAA[A/G]CCGGT | 28,922,005 | 28,922,093 | 28,922,088 | 0.000867 | G/G | A/A | 2 |
| Melon_sbg_20578_63 | CTTTGTCGAAAGCGTATGAACGCCGTGCGAGTGAAATTCAATTTATGAAACCAATAAATTCA[A/T]AGAAGAATAATAAACATGCTTCTCAT | 29,092,886 | 29,092,974 | 29,092,967 | 0.000418 | A/A | T/T | 3 |
| Melon_sbg_20578_82 | CTTTGTCGAAAGCGTATGAACGCCGTGCGAGTGAAATTCAATTTATGAAACCAATAAATTCAAAGAAGAATAAACATG[C/A]TTCTCAT | 29,092,886 | 29,092,974 | 29,092,948 | 0.000418 | C/C | A/A | 4 |
| Melon_sbg_55680_17 | GACAACCAACTTTACC[G/A]ATAACCTTCCCGATCTGCTTGGAGGGCACAACGATTCTGAAAAGCACGTCGTGGGCCTTCGCTTGTCTTTTA | 29,307,652 | 29,307,740 | 29,307,668 | 0.000878 | A/A | G/G | 5 |
| Melon_sbg_60684_74 | TATCCCTCCACTCGTCTCATTTATGATGTCCTCCTTTGGGTGTTTGGGTGCACAACCTATGTTCTTAGCCATG[G/A]TCCTAACCAAACTAA | 29,618,689 | 29,618,777 | 29,618,762 | 8.671E-05 | A/A | G/G | 6 |
| Melon_sbg_33761_74 | CTCAGATAATCAACCTCTGTACGACTGGCCTAATGGTCGGAACTTCAACATCATCCAACACCAGCTCGGCAA[C/T]GTTCTCTACGACCTC | 30,171,021 | 30,171,109 | 30,171,094 | 3.580E-07 | T/T | C/C | 7 |
| Melon_sbg_2720_78 | AACCAACACTGTTTCTTGTGAAAATTGTTTGGTTGTTATATCTGTATGCAGAGGCCTATTATGTGGTGCTTTGATGG[G/A]TGGTTTAGAAT | 30,328,018 | 30,328,106 | 30,328,095 | 7.282E-07 | G/G | A/A | 8 |
| Melon_sbg_14207_58 | GGCCTAAAAAATCGTAGCATTATAGAGAAATGCAAACAAGGGTAGAAGGGTAGAAG[C/A]GCTTGCCTTGTACAAGAACTCCGCATAGTTA | 30,335,962 | 30,336,050 | 30,336,019 | 2.523E-07 | A/A | C/C | 9 |
| Melon_sbg_22016_27 | CCACCTGAAGACGTGGAGATCCAACG[G/C]TCGAGATCGAACCGTAACGGCCTCGCCAAATCCAACGGCAAAAACTAGCGAAAGTGGAAG | 30,391,940 | 30,392,028 | 30,391,966 | 3.437E-06 | G/G | C/C | 10 |
| Melon_sbg_22016_30 | CCACCTGAAGACGTGGAGATCCAACGGT[G/A]AGATCGAACCGTAACGGCCTCGCCAAATCCAACGGCAAAAACTAGCGAAAGTGGAAG | 30,391,940 | 30,392,028 | 30,391,969 | 3.437E-06 | G/G | A/A | 11 |

TABLE 4-continued

SNPs linked to ToLCNDV resistance, location and flanking sequences:
Loc: Location on chromosome 11-Nt R: Nucleotide in resistant bulk, corresponding to alleles of H-MLCND-32. Nt S: Nucleotide in susceptible bulk. It must be borne in mind that, outside the introgression fragment of the invention, delimited by SNP Melon_sbg_617_42 and Melon_sbg_16835_17, preferably by Melon_sbg_33761_74 and Melon_sbg_22016_36, the association with susceptible/resistance phenotype is very low.

| SNP | Sequence surrounding the SNP | Left border | Right border | SNP position | P-Value | Nt R | Nt S | Seq ID |
|---|---|---|---|---|---|---|---|---|
| Melon_sbg_22016_36 | CCACCTGAAGACGTGAGATCCAACGGTCGA GATC[G/A]AACCGTAACGGCCTCGCCAAAATC CAACGGCAAAAACTAGCGAAAGTGGAAG | 30,391,940 | 30,392,028 | 30,391,975 | 3.437E-06 | G/G | A/A | 12 |
| Melon_sbg_11556_13 | TCGAGCCAAAGA[C/T]TGAAGATCACCATCTT CACCCATCTGATCTTGATAATCAACTGGGTTC AGAAAGCTATTTGTCATTTCGTTACAAC | 31,136,530 | 31,136,618 | 31,136,542 | 8.788E-05 | C/C | T/T | 13 |
| Melon_sbg_24259_45 | TGGTGGGATTTGAATCCAAGATGTCTGTCAGT GCTTCCTCTTCA[C/G]ACCCGCAGGGATTGGAC AAAAGCCGACAGCGCGGTGATGCGCCG | 31,159,064 | 31,159,152 | 31,159,108 | 8.788E-05 | C/C | G/G | 14 |
| Melon_sbg_16835_5 | CCAG[C/T][GGTCTTCTCGGCGGCGGCGATT GAGTCTACACTCCGGTTTTCAACTCCGACGC AGGGCTGCAAATTTGATTATCGAGGGAAAA | 31,209,200 | 31,209,288 | 31,209,204 | 8.788E-05 | T/T | C/C | 15 |
| Melon_sbg_16835_17 | CCAGGGTGTTCGTCG[G/T]CGGCGGCGATT GAGTCTACACTCCGGTTTTCAACTCCGACGC AGGGCTGCAAATTTGATTATCGAGGGAAAA | 31,209,200 | 31,209,288 | 31,209,216 | 5.811E-05 | T/T | G/G | 16 |

Seeds of RILs 69 and 82 have been deposited by Hazera Seeds Ltd, Berurim, M. P. Shikmim 79837, Israel, with the NCIMB (NCIMB Ltd, Ferguson Building, Craibstone Estate, Bucksburn, Aberdeen AB21 9YA, United Kingdom), on 23 Dec. 2015, under the name ToLR1 and accession number NCIMB 42506. Some of their characteristics are studied in example 10. They are also characterized by the following features: the flower female distribute along the shoots, the shoots are not thin and long as in the wild-types. The RILs set at internode 8-15 similar to cultural plants, there is no strong branching.

TABLE 5

| SNP | RIL-30 | RIL-69 | RIL-82 | H-MLCND-32 |
|---|---|---|---|---|
| Melon_sbg_2869_86 | T/T | T/T | T/T | T/T |
| Melon_sbg_3859_5 | G/G | T/T | T/T | T/T |
| Melon_sbg_21303_5 | G/G | T/T | T/T | T/T |
| Melon_sbg_15226_34 | A/A | T/T | T/T | T/T |
| Melon_sbg_40291_40 | NA | A/A | A/A | A/A |
| Melon_sbg_8091_11 | T/T | C/C | C/C | C/C |
| Melon_sbg_29917_65 | C/C | G/G | G/G | G/G |
| Melon_sbg_1548_24 | A/A | T/T | T/T | T/T |
| Melon_sbg_22966_49 | NA | A/A | NA | A/A |
| Melon_sbg_22966_72 | NA | G/G | NA | G/G |
| Melon_sbg_617_42 | G/G | T/T | T/T | T/T |
| Melon_sbg_617_84 | A/A | G/G | G/G | G/G |
| Melon_sbg_20578_63 | T/T | A/A | A/A | A/A |
| Melon_sbg_20578_82 | A/A | C/C | C/C | C/C |
| Melon_sbg_55680_17 | G/G | A/A | A/A | A/A |
| Melon_sbg_60684_74 | NA | A/A | A/A | A/A |
| Melon_sbg_33761_74 | T/T | T/T | T/T | T/T |
| Melon_sbg_2720_78 | G/G | G/G | G/G | G/G |
| Melon_sbg_14207_58 | A/A | A/A | A/A | A/A |
| Melon_sbg_22016_27 | G/G | G/G | G/G | G/G |
| Melon_sbg_22016_30 | G/G | G/G | G/G | G/G |
| Melon_sbg_22016_36 | G/G | G/G | G/G | G/G |
| Melon_sbg_11556_13 | C/C | C/C | C/C | C/C |
| Melon_sbg_24259_45 | C/C | C/C | C/C | C/C |
| Melon_sbg_16835_5 | T/T | T/T | T/T | T/T |
| Melon_sbg_16835_17 | T/T | T/T | T/T | T/T |

Example 9: Marker Prediction Value

FIG. 3 is a mosaic plot showing frequencies of phenotypes for each genotypic group determined by Melon_sbg_14207_58 (SEQ ID No:9). Over all this SNP predicts the phenotype of 81% from RIL.

Example 10: *Cucumis melo* Subsp *melo* Plants Resistant to ToLCNDV

Once the resistance has been identified, the present inventors have been able to obtain *Cucumis melo* subsp *melo* plants resistant to ToLCNDV that do not harbor the phenotypic characteristics of the original *Cucumis melo* subsp *agrestis* var. *acidulous* plant, especially in terms of brix and flesh color.

Table 6 illustrates the phenotypic trait of these plants.

TABLE 6

| Plant | Resistance to ToLCNDV | Brix | Fruit shape | Flesh color |
|---|---|---|---|---|
| RIL-30 | Resistant | 12 | Oval | OR1 |
| RIL-66 | Resistant | 9 | Oval | White green |
| RIL 69 | Resistant | 9 | Round-Oval | OR1 |
| RIL 82 | Resistant | 10 | Oval | OR-Crm |
| Vedrantais | Susceptible | 12 | Round | OR1-OR2 |
| H-MLCND-32 | Resistant | 5.5 | Oval | White green |

In table 6, OR1 "standard orange" is the standard color of orange flesh in commercial melon.

OR-Crm means that a mix color is in the flesh (patches of cream color).

The scale of orange—from light to dark:

OR0—light orange; OR1—standard orange; OR2—deep orange; OR3—very deep orange

A genetic analysis demonstrates that the resistant plants harbor the introgressed sequences containing the resistance as evidenced by the presence of the SNP identified by the present inventors.

| Plant | Melon_sbg_22016_27 | Melon_sbg_14207_58 | Melon_sbg_2720_78 |
|---|---|---|---|
| RIL 30 | G/G | A/A | G/G |
| RIL 66 | G/G | A/A | G/G |
| RIL69 | G/G | A/A | G/G |
| RIL82 | G/G | A/A | G/G |
| Vedrantais | C/C | C/C | A/A |
| H-MLCND-32 | G/G | A/A | G/G |

REFERENCES

Fauquet, C. M., Briddon, R. W., Brown, J. K., Moriones, E., Stanley, J., Zerbini, M., and Zhou, X., 2008. Geminivirus strain demarcation and nomenclature. Arch. Virol. 153: 783-821.

Funayama, S. 2001. Effects of Virus Infection and Light Environment on Population Dynamics of Eupatorium makinoi (Asteraceae). American Journal of Botany 88: 616.

Garcia-Mas, J. et al. 2012. The genome of melon (Cucumis melo L.). Proc Natl Acad Sci USA. 109(29):11872-7.

Islam, S. et al. 2011. Screening of Luffa cylindrica Roem against tomato leaf curl New Delhi virus, inheritance of resistance and identification of SRAP markers linked to resistance gene. Journal of Horticulture Science and Biotechnology 86(6):661-667.

Kirkbride, J. H., Jr. 1993. Biosystematic monograph of the genus Cucumis (Cucurbitaceae). 84.

Lopez, C. et al. 2015. Mechanical transmission of Tomato leaf curl New Delhi virus to cucurbit germplasm: selection of tolerance sources in Cucumis melo. Eupphytica 204:679-691

Pitrat, M. P. Hanelt and K. Hammer. 2000. Some comments on intraspecific classification of cultivars of melon. Acta Hort. 510:29-36.

Ruiz L. et al. 2006. Analysis of the temporal and spatial disease progress of Bemisia tabaci-transmitted Cucurbit yellow stunting disorder virus and Cucumber vein yellowing virus in cucumber. Plant Pathology 55(2): 264-275.

Ruiz L. et al. 2015. First Report of Tomato leaf curl New Delhi virus Infecting Tomato in Spain. Plant Disease 99(6):684.

Saeed M. et al. 2007. A monopartite begomovirus-associated DNA beta satellite substitutes for the DNA B of a bipartite begomovirus to permit systemic infection. J Gen Virol. 88(Pt 10):2881-9.

---

The invention claimed is:

1. A *Cucumis melo* subsp. *melo* plant resistant to Tomato leaf curl New Delhi virus (ToLCNDV), having in its genome introgressed sequences from *C. melo* subsp. *agrestis* var. *acidulous*, conferring said resistance only when present homozygously,
wherein said introgressed sequences are: (1) located on homologous chromosome 11, within the chromosomal region delimited by (a) SNP Melon_sbg_33761_74, the sequence of which is set forth in SEQ ID No:7, and (b) SNP Melon_sbg_22016_36, the sequence of which is set forth in SEQ ID No:12, and (2) the same as the sequence present in the genome of a resistant *C. melo* seed, deposited as NCIMB accession number NCIMB-42506, on chromosome 11 within the chromosomal region delimited by SNP Melon_sbg_33761_74 and SNP Melon_sbg_22016_36.

2. The plant according to claim 1, wherein the presence of said introgressed sequences on chromosome 11 and conferring said resistance is characterized by at least one marker selected from the group consisting of SNP Melon_sbg_33761_74, the sequence of which is set forth in SEQ ID No:7, SNP Melon_sbg_2720_78, the sequence of which is set forth in SEQ ID No:8, SNP Melon_sbg_14207_58, the sequence of which is set forth in SEQ ID No:9, SNP Melon_sbg_22016_27, the sequence of which is set forth in SEQ ID No:10, SNP Melon_sbg_22016_30, the sequence of which is set forth in SEQ ID No:11, and SNP Melon_sbg_22016_36, the sequence of which is set forth in SEQ ID No:12.

3. The plant according to claim 2, wherein the presence of said introgressed sequence is characterized by the presence of allele T of SNP Melon_sbg_33761_74 and/or the presence of allele G of SNP Melon_sbg_2720_78 and/or the presence of allele A of SNP Melon_sbg_14207_58 and/or the presence of allele G of SNP Melon_sbg_22016_27 and/or the presence of allele G of SNP Melon_sbg_22016_30 and/or the presence of allele G of SNP Melon_sbg_22016_36.

4. The plant according to claim 1, wherein the presence of said introgressed sequences on homologous chromosome 11 is characterized by:
   a) the detection of allele T of SNP Melon_sbg_33761_74 combined with the lack of detection of allele C for said SNP; and/or
   b) the detection of allele G of SNP Melon_sbg_2720_78 combined with the lack of detection of allele A for said SNP; and/or
   c) the detection of allele A of SNP Melon_sbg_14207_58 combined with the lack of detection of allele C for said SNP; and/or d) the detection of allele G of SNP Melon_sbg_22016_27 combined with the lack of detection of allele C for said SNP; and/or
e) the detection of allele G of SNP Melon_sbg_22016_30 combined with the lack of detection of allele A for said SNP; and/or
f) the detection of allele G of SNP Melon_sbg_22016_36 combined with the lack of detection of allele A for said SNP.

5. The plant according to claim 1, wherein said plant is a progeny of, or is derived from a deposited seed under NCIMB accession number 42506.

6. A Hybrid plant of *Cucumis melo* subsp. *melo*, obtained by crossing a plant resistant to ToLCNDV according to claim 1 with another *C. melo* subsp. *melo*.

7. The plant according to claim 1, wherein said plant can bear marketable melon fruits.

8. A cell of a *Cucumis melo* subsp. *melo* plant according to claim 1, comprising in its genome introgressed sequences from *C. melo* subsp. *agrestis* var. *acidulous* on chromosome 11, wherein said introgressed sequences: (1) confer resistance to ToLCNDV only when present homozygously on homologous chromosome 11, within the chromosomal region delimited by (a) SNP Melon_sbg_33761_74, the sequence of which is set forth in SEQ ID No:7, and (b) SNP Melon_sbg_22016_36, the sequence of which is set forth in SEQ ID No:12, and (2) are the same as the sequence present in the genome of a resistant *C. melo* seed, deposited as NCIMB accession number NCIMB-42506, on chromosome 11 within the chromosomal region delimited by SNP Melon_sbg_33761_74 and SNP Melon_sbg_22016_36.

9. A plant part, explant, scion, cutting, seed, fruit, root, rootstock, pollen, ovule, embryo, siliqua, protoplast, leaf, anther, stem or petiole of a *C. melo* subsp. *melo* plant having in its genome introgressed sequences conferring resistance to ToLCNDV only when present homozygously,
wherein said plant part, explant, scion, cutting, seed, fruit, root, rootstock, pollen, ovule, embryo, siliqua, protoplast, leaf, anther, stem or petiole is obtained from a plant according to claim 1 and comprises cells comprising in their genome introgressed sequences from *C. melo* subsp. *agrestis* var. *acidulous* on chromosome 11, wherein said introgressed sequences: (1) confer resistance to ToLCNDV only when present homozygously on homologous chromosome 11, within the chromosomal region delimited by (a) SNP Melon_sbg_33761_74, the sequence of which is set forth in SEQ ID No:7, and (b) SNP Melon_sbg_22016_36, the sequence of which is set forth in SEQ ID No:12, and (2) are the same as the sequence present in the genome of a resistant *C. melo* seed, deposited as NCIMB accession number NCIMB-42506, on chromosome 11 within the chromosomal region delimited by SNP Melon_sbg_33761_74 and SNP Melon_sbg_22016_36.

10. A seed of a *Cucumis melo* subsp. *melo* plant, giving rise when grown up to a plant according to claim 1.

11. A tissue culture of regenerable cells of the plant according to claim 1, wherein the regenerable cells are derived from embryos, protoplasts, meristematic cells, callus, pollen, leaves, anthers, stems, petioles, roots, root tips, siliqua, seeds, flowers, cotyledons, and/or hypocotyls, and contain in their genome introgressed sequences from *C. melo* subsp. *agrestis* var. *acidulous* on chromosome 11 conferring resistance to ToLCNDV only when present homozygously, wherein said introgressed sequences: (1) are located on homologous chromosome 11, within the chromosomal region delimited by (a) SNP Melon_sbg_33761_74, the sequence of which is set forth in SEQ ID No:7, and (b) SNP Melon_sbg_22016_36, the sequence of which is set forth in SEQ ID No:12, and (2) are the same as the sequence present in the genome of a resistant *C. melo* seed, deposited as NCIMB accession number NCIMB-42506, on chromosome 11 within the chromosomal region delimited by SNP Melon_sbg_33761_74 and SNP Melon_sbg_22016_36.

12. The seed or plant part according to claim 9, wherein the presence of said introgressed sequences on chromosome 11 is characterized by:
a) the presence of allele T of SNP Melon_sbg_33761_74; and/or
b) the presence of allele G of SNP Melon_sbg_2720_78; and/or
c) the presence of allele A of SNP Melon_sbg_14207_58; and/or
d) the presence of allele G of SNP Melon_sbg_22016_27; and/or
e) the presence of allele G of SNP Melon_sbg_22016_30; and/or
f) the presence of allele G of SNP Melon_sbg_22016_36.

13. A method for detecting and selecting *C. melo* subsp. *melo* plants according to claim 1, comprising detecting at least one of the following markers: allele T of SNP Melon_sbg_33761_74 and/or allele G of SNP Melon_sbg_2720_78 and/or allele A of SNP Melon_sbg_14207_58 and/or allele G of SNP Melon_sbg_22016_27 and/or allele G of SNP Melon_sbg_22016_30 and/or allele G of SNP Melon_sbg_22016_36, in a sample of genetic material from such plants, and selecting plants in which at least one such marker is detected.

14. A method for breeding *Cucumis melo* subsp. *melo* plants resistant to ToLCNDV, comprising the steps of crossing a plant grown from the deposited seeds NCIMB 42506 or progeny thereof bearing the sequences conferring the resistance to ToLCNDV, with a *Cucumis melo* subsp. *melo* plant susceptible or less resistant to ToLCNDV, wherein said sequences are located on homologous chromosome 11, within the chromosomal region delimited by (a) SNP Melon_sbg_33761_74, the sequence of which is set forth in SEQ ID No:7, and (b) SNP Melon_sbg_22016_36, the sequence of which is set forth in SEQ ID No:12, and are introgressed from the deposited seeds NCIMB 42506.

15. A method for the production of *Cucumis melo* subsp. *melo* plants resistant to ToLCNDV, comprising the steps of:
a) crossing a plant grown from the deposited seeds NCIMB 42506, or progeny thereof bearing the sequences conferring the resistance to ToLCNDV, and a susceptible or less resistant *Cucumis melo* subsp. *melo* plant, wherein said sequences are located on homologous chromosome 11, within the chromosomal region delimited by (a) SNP Melon_sbg_33761_74, the sequence of which is set forth in SEQ ID No:7, and (b) SNP Melon_sbg_22016_36, the sequence of which is set forth in SEQ ID No:12, and are introgressed from the deposited seeds NCIMB 42506;
b) selecting a plant in the progeny thus obtained bearing sequences conferring resistance to ToLCNDV only when present homozygously;
c) self-pollinating one or several times the plant obtained at step b) and selecting a resistant plant in the progeny thus obtained.

16. The method of claim 15, wherein SNPs markers are used in steps b) and/or c) for selecting plants bearing sequences conferring resistance to ToLCNDV only when present homozygously and/or plants resistant to ToLCNDV.

17. A method for the production of *Cucumis melo* subsp. *melo* plants resistant to ToLCNDV comprising the steps of:
- a1) crossing a plant grown from the deposited seeds NCIMB 42506 or progeny thereof bearing the sequences conferring the resistance to ToLCNDV, and a susceptible or less resistant *C. melo* subsp. *melo* plant, thus generating the F1 population, wherein said sequences are located on homologous chromosome 11, within the chromosomal region delimited by (a) SNP Melon_sbg_33761_74, the sequence of which is set forth in SEQ ID No:7, and (b) SNP Melon_sbg_22016_36, the sequence of which is set forth in SEQ ID No:12, and are introgressed from the deposited seeds NCIMB 42506,
- a2) advancing the F1 population to create F2 population,
- b) selecting resistant individuals in the progeny thus obtained;
- c) optionally self-pollinating one or several times the resistant plant obtained at step b) and selecting a resistant plant in the progeny thus obtained;
- d) optionally backcrossing the resistant plant selected in step b) or c) with a *Cucumis melo* subsp. *melo* plant susceptible to ToLCNDV infection,
- e) selecting in the progeny a plant bearing sequences linked to the resistance to ToLCNDV,
- f) self-pollinating the plant obtained at step e) or crossing distinct plants obtained at step e), one or several times, and
- g) selecting a plant resistant to ToLCNDV.

18. The method of claim 17, wherein SNPs markers are used for selecting plants bearing the introgressed sequences linked to resistance to ToLCNDV only when present homozygously or for selecting plants resistant to ToLCNDV.

19. The method according to claim 14, wherein the selection is carried out by detection of at least one of the following alleles: allele T of SNP Melon_sbg_33761_74, allele G of SNP Melon_sbg_2720_78, allele A of SNP Melon_sbg_14207_58, allele G of SNP Melon_sbg_22016_27, allele G of SNP Melon_sbg_22016_30 and allele G of SNP Melon_sbg_22016_36.

20. The method according to claim 14, wherein the selection of a resistant plant is carried out by the detection of:
- a) the presence of allele T of SNP Melon_sbg_33761_74 combined with the absence of allele C for said SNP; and/or
- b) the presence of allele G of SNP Melon_sbg_2720_78 combined with the absence of allele A for said SNP; and/or
- c) the presence of allele A of SNP Melon_sbg_14207_58 combined with the absence of allele C for said SNP; and/or
- d) the presence of allele G of SNP Melon_sbg_22016_27 combined with the absence of allele C for said SNP; and/or
- e) the presence of allele G of SNP Melon_sbg_22016_30 combined with the absence of allele A for said SNP; and/or
- f) the presence of allele G of SNP Melon_sbg_22016_36 combined with the absence of allele A for said SNP.

* * * * *

UNITED STATES PATENT AND TRADEMARK OFFICE
CERTIFICATE OF CORRECTION

PATENT NO. : 10,939,628 B2
APPLICATION NO. : 16/066593
DATED : March 9, 2021
INVENTOR(S) : Paz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

Signed and Sealed this
Twenty-first Day of February, 2023

Katherine Kelly Vidal
*Director of the United States Patent and Trademark Office*

SEQUENCE LISTING

```
<160> NUMBER OF SEQ ID NOS: 26

<210> SEQ ID NO 1
<211> LENGTH: 89
<212> TYPE: DNA
<213> ORGANISM: Cucumis melo
<220> FEATURE:
<221> NAME/KEY: polymorphism
<222> LOCATION: (42)..(42)
<223> OTHER INFORMATION: susceptible = G ; resistant = T

<400> SEQUENCE: 1
aaccaaagta cctgttgggg ctctttcccg tcaatccggt ckggctccgc atgtgccaca      60
gctacaatgt ggcgtctggc caaaccggt                                       89

<210> SEQ ID NO 2
<211> LENGTH: 89
<212> TYPE: DNA
<213> ORGANISM: Cucumis melo
<220> FEATURE:
<221> NAME/KEY: polymorphism
<222> LOCATION: (84)..(84)
<223> OTHER INFORMATION: susceptible = A ; resistant = G

<400> SEQUENCE: 2
aaccaaagta cctgttgggg ctctttcccg tcaatccggt cgggctccgc atgtgccaca      60
gctacaatgt ggcgtctggc caarccggt                                       89

<210> SEQ ID NO 3
<211> LENGTH: 89
<212> TYPE: DNA
<213> ORGANISM: Cucumis melo
<220> FEATURE:
<221> NAME/KEY: polymorphism
<222> LOCATION: (63)..(63)
<223> OTHER INFORMATION: susceptible = T ; resistant = A

<400> SEQUENCE: 3
ctttgtcgaa agcgtatgaa cgccgtgcga gtgaaattca atttatgaaa ccaataaatt      60
cawagaagaa taataaacat gcttctcat                                       89

<210> SEQ ID NO 4
<211> LENGTH: 89
<212> TYPE: DNA
```

```
<213> ORGANISM: Cucumis melo
<220> FEATURE:
<221> NAME/KEY: polymorphism
<222> LOCATION: (82)..(82)
<223> OTHER INFORMATION: susceptible = A ; resistant = C

<400> SEQUENCE: 4
ctttgtcgaa agcgtatgaa cgccgtgcga gtgaaattca atttatgaaa ccaataaatt      60
caaagaagaa taataaacat gmttctcat                                       89

<210> SEQ ID NO 5
<211> LENGTH: 89
<212> TYPE: DNA
<213> ORGANISM: Cucumis melo
<220> FEATURE:
<221> NAME/KEY: polymorphism
<222> LOCATION: (17)..(17)
<223> OTHER INFORMATION: susceptible = G ; resistant = A

<400> SEQUENCE: 5
gacaaccaac tttaccrata accttcccga tctgcttgga gggcacaacg attctgaaaa      60
gcacgtcgtg ggccttcgct tgtcttta                                        89

<210> SEQ ID NO 6
<211> LENGTH: 89
<212> TYPE: DNA
<213> ORGANISM: Cucumis melo
<220> FEATURE:
<221> NAME/KEY: polymorphism
<222> LOCATION: (74)..(74)
<223> OTHER INFORMATION: susceptible = G ; resistant = A

<400> SEQUENCE: 6
tatccctcca ctcgtctcat ttatgatgtc ctcctttggg tgtttgggtg cacaacctat      60
gttcttagcc atgrtcctaa ccaaactaa                                       89

<210> SEQ ID NO 7
<211> LENGTH: 89
<212> TYPE: DNA
<213> ORGANISM: Cucumis melo
<220> FEATURE:
<221> NAME/KEY: polymorphism
<222> LOCATION: (74)..(74)
<223> OTHER INFORMATION: susceptible = C ; resistant = T

<400> SEQUENCE: 7
ctcagataat caacctctgg tacgactggc ctaatggtcg gaacttcaac atcatccaac      60
accagctcgg caaygttctc tacgacctc                                       89

<210> SEQ ID NO 8
<211> LENGTH: 89
<212> TYPE: DNA
<213> ORGANISM: Cucumis melo
<220> FEATURE:
<221> NAME/KEY: polymorphism
<222> LOCATION: (78)..(78)
<223> OTHER INFORMATION: susceptible = A ; resistant = G

<400> SEQUENCE: 8
aaccaacact gtttcttgtg aaaattgttt ggttgttata tctgtatgca gaggcctatt      60
atgtggtgct ttgatggrtg gtttagaat                                       89

<210> SEQ ID NO 9
<211> LENGTH: 89
```

```
<212> TYPE: DNA
<213> ORGANISM: Cucumis melo
<220> FEATURE:
<221> NAME/KEY: polymorphism
<222> LOCATION: (58)..(58)
<223> OTHER INFORMATION: susceptible = C ; resistant = A

<400> SEQUENCE: 9
ggcctaaaaa aatcgtagca ttatagagaa atgcaaacaa gggtagaagg gtagaagmgc       60
ttgccttgta caagaactcc gcatagtta                                          89

<210> SEQ ID NO 10
<211> LENGTH: 89
<212> TYPE: DNA
<213> ORGANISM: Cucumis melo
<220> FEATURE:
<221> NAME/KEY: polymorphism
<222> LOCATION: (27)..(27)
<223> OTHER INFORMATION: susceptible = C ; resistant = G

<400> SEQUENCE: 10
ccacctgaag acgtggagat ccaacgstcg agatcgaacc gtaacggcct cgccaaaatc       60
caacggcaaa aaactagcga aagtggaag                                          89

<210> SEQ ID NO 11
<211> LENGTH: 89
<212> TYPE: DNA
<213> ORGANISM: Cucumis melo
<220> FEATURE:
<221> NAME/KEY: polymorphism
<222> LOCATION: (30)..(30)
<223> OTHER INFORMATION: susceptible = A ; resistant = G

<400> SEQUENCE: 11
ccacctgaag acgtggagat ccaacggtcr agatcgaacc gtaacggcct cgccaaaatc       60
caacggcaaa aaactagcga aagtggaag                                          89

<210> SEQ ID NO 12
<211> LENGTH: 89
<212> TYPE: DNA
<213> ORGANISM: Cucumis melo
<220> FEATURE:
<221> NAME/KEY: polymorphism
<222> LOCATION: (36)..(36)
<223> OTHER INFORMATION: susceptible = A ; resistant = G

<400> SEQUENCE: 12
ccacctgaag acgtggagat ccaacggtcg agatcraacc gtaacggcct cgccaaaatc       60
caacggcaaa aaactagcga aagtggaag                                          89

<210> SEQ ID NO 13
<211> LENGTH: 89
<212> TYPE: DNA
<213> ORGANISM: Cucumis melo
<220> FEATURE:
<221> NAME/KEY: polymorphism
<222> LOCATION: (13)..(13)
<223> OTHER INFORMATION: susceptible = T ; resistant = C

<400> SEQUENCE: 13
tcgagccaaa gaytgaagat caccatcttc acccatctga tcttgataat caactgggtt       60
cagaaagcta tttgtcattt cgttacaac                                          89

<210> SEQ ID NO 14
```

```
<211> LENGTH: 89
<212> TYPE: DNA
<213> ORGANISM: Cucumis melo
<220> FEATURE:
<221> NAME/KEY: polymorphism
<222> LOCATION: (45)..(45)
<223> OTHER INFORMATION: susceptible = G ; resistant = C

<400> SEQUENCE: 14
tggtgggatt tgaatccaag atgtctgtca gtgcttcctc ttcasaccgc agggattgga      60
caaaagccgg acagcgcggt gatgcgccg                                       89

<210> SEQ ID NO 15
<211> LENGTH: 89
<212> TYPE: DNA
<213> ORGANISM: Cucumis melo
<220> FEATURE:
<221> NAME/KEY: polymorphism
<222> LOCATION: (5)..(5)
<223> OTHER INFORMATION: susceptible = C ; resistant = T

<400> SEQUENCE: 15
ccagyggtct tcgtcggcgg cggcgattga gtctacactc cggttttcaa ctccgacgca      60
gggctgcaaa tttgattatc gagggaaaa                                       89

<210> SEQ ID NO 16
<211> LENGTH: 89
<212> TYPE: DNA
<213> ORGANISM: Cucumis melo
<220> FEATURE:
<221> NAME/KEY: polymorphism
<222> LOCATION: (17)..(17)
<223> OTHER INFORMATION: susceptible = G ; resistant = T

<400> SEQUENCE: 16
ccagcggtct tcgtcgkcgg cggcgattga gtctacactc cggttttcaa ctccgacgca      60
gggctgcaaa tttgattatc gagggaaaa                                       89

<210> SEQ ID NO 17
<211> LENGTH: 89
<212> TYPE: DNA
<213> ORGANISM: Cucumis melo
<220> FEATURE:
<221> NAME/KEY: polymorphism
<222> LOCATION: (86)..(86)
<223> OTHER INFORMATION: susceptible = C ; resistant = T

<400> SEQUENCE: 17
tcacgccgtg ttttcaacgc acaaattgaa tttccgacac ccttatatta ttatcacctc      60 cactcccccca ccgccgccgc ctctcycgc                                      89

<210> SEQ ID NO 18
<211> LENGTH: 89
<212> TYPE: DNA
<213> ORGANISM: Cucumis melo
<220> FEATURE:
<221> NAME/KEY: polymorphism
<222> LOCATION: (5)..(5)
<223> OTHER INFORMATION: susceptible = G  ; resistant =  T

<400> SEQUENCE: 18
accgkcgact cattggtccg gcgacagagg agagagagag agattgatgc tcaagcgtgc      60
gagcatgcga ggggaagggg ttcgcacgc                                       89
```

<210> SEQ ID NO 19
<211> LENGTH: 89
<212> TYPE: DNA
<213> ORGANISM: Cucumis melo
<220> FEATURE:
<221> NAME/KEY: polymorphism
<222> LOCATION: (5)..(5)
<223> OTHER INFORMATION: susceptible = G ; resistant = T

<400> SEQUENCE: 19
accgkcgact cattggtccg gcgacagagg agagagagag attgatgctc aagcgtgcga    60
gcatgcgagg ggaaggggtt cgcacgcgc                                      89

<210> SEQ ID NO 20
<211> LENGTH: 89
<212> TYPE: DNA
<213> ORGANISM: Cucumis melo
<220> FEATURE:
<221> NAME/KEY: polymorphism
<222> LOCATION: (34)..(34)
<223> OTHER INFORMATION: susceptible = A ; resistant = T

<400> SEQUENCE: 20
gaggcagtct tctccccatg tagacttcat tctwcccgtg gaatagatcg aatacgtaac    60
cgatgatccc gccggaacga aggttccgt                                      89

<210> SEQ ID NO 21
<211> LENGTH: 89
<212> TYPE: DNA
<213> ORGANISM: Cucumis melo
<220> FEATURE:
<221> NAME/KEY: polymorphism
<222> LOCATION: (40)..(40)
<223> OTHER INFORMATION: susceptible = T ; resistant = A

<400> SEQUENCE: 21
gcacccgatt gatcttcaag acgtgttgtt acgtcttacw tttgataata tttgtggttt    60
ggcttttgga aaagatccaa tgacttgtg                                      89

<210> SEQ ID NO 22
<211> LENGTH: 89
<212> TYPE: DNA
<213> ORGANISM: Cucumis melo
<220> FEATURE:
<221> NAME/KEY: polymorphism
<222> LOCATION: (11)..(11)
<223> OTHER INFORMATION: susceptible = T ; resistant = C

<400> SEQUENCE: 22
accggggcgg yggctttcag gacgttgaag gaaaatgaat ggaccaaacg agaacgacca    60
aagtgggtcg acgtccaaat cagcatttc                                      89

<210> SEQ ID NO 23
<211> LENGTH: 89
<212> TYPE: DNA
<213> ORGANISM: Cucumis melo
<220> FEATURE:
<221> NAME/KEY: polymorphism
<222> LOCATION: (65)..(65)
<223> OTHER INFORMATION: susceptible = C ; resistant = G

<400> SEQUENCE: 23
ggagcaatgc gacgacgccg tcaccgtctg acgtggagga gttggattat gtggaagacg    60
atgasgacga tgaggaggag gaggacggc                                      89

```
<210> SEQ ID NO 24
<211> LENGTH: 89
<212> TYPE: DNA
<213> ORGANISM: Cucumis melo
<220> FEATURE:
<221> NAME/KEY: polymorphism
<222> LOCATION: (24)..(24)
<223> OTHER INFORMATION: susceptible = A ; resistant = T

<400> SEQUENCE: 24
cacggctgca ttcctagcac catwggccaa atgtctaacc tcaaccaaat tctctttctc      60
ggcaacaagc tcggtggttg tttcccacc                                         89

<210> SEQ ID NO 25
<211> LENGTH: 89
<212> TYPE: DNA
<213> ORGANISM: Cucumis melo
<220> FEATURE:
<221> NAME/KEY: polymorphism
<222> LOCATION: (49)..(49)
<223> OTHER INFORMATION: susceptible = G ; resistant = A

<400> SEQUENCE: 25
ttgtttggag agtctggctt gcggcgttcc aaccgtggcg tttccacart ggtccgatca      60
agcgaccaac actaagatca ttcaggact                                         89

<210> SEQ ID NO 26
<211> LENGTH: 89
<212> TYPE: DNA
<213> ORGANISM: Cucumis melo
<220> FEATURE:
<221> NAME/KEY: polymorphism
<222> LOCATION: (72)..(72)
<223> OTHER INFORMATION: susceptible = C ; resistant = G

<400> SEQUENCE: 26
ttgtttggag agtctggctt gcggcgttcc aaccgtggcg tttccacagt ggtccgatca      60
agcgaccaac astaagatca ttcaggact                                         89
```